United States Patent [19]
Kimura et al.

[11] Patent Number: 5,690,916
[45] Date of Patent: Nov. 25, 1997

[54] SKIN-COLOR ADJUSTING METHOD, SKIN-COLOR ADJUSTING COMPOSITION AND COLORED TITANIUM OXIDE COATED MICA USED THEREFOR

[75] Inventors: Asa Kimura, Yokohama; Toshihiro Tanaka, Tokyo; Mari Yoshida; Yoshiaki Yagita, both of Yokohama, all of Japan

[73] Assignee: Shiseido Co., Ltd., Tokyo, Japan

[21] Appl. No.: 528,110

[22] Filed: Sep. 14, 1995

[30] Foreign Application Priority Data

| Sep. 14, 1994 | [JP] | Japan | 6-243714 |
| Sep. 14, 1994 | [JP] | Japan | 6-247315 |
| Sep. 14, 1994 | [JP] | Japan | 6-247316 |

[51] Int. Cl.$^6$ ............ A61K 7/42; A61K 7/00; C04B 14/00
[52] U.S. Cl. ............ 424/59; 424/60; 424/400; 424/401; 106/418; 106/428; 106/436; 106/439
[58] Field of Search ............ 424/59, 60, 400, 424/401; 106/418, 428, 436, 439

[56] References Cited

U.S. PATENT DOCUMENTS 4,650,672 3/1987 Yagita ............ 424/69
5,176,905 1/1993 Ohno ............ 424/69

*Primary Examiner*—Shelley A. Dodson
*Attorney, Agent, or Firm*—Ronald R. Snider

[57] ABSTRACT

In order to make a hyperchromic portion of the skin, which has been caused by nevus, angioma, red face, spots, freckles, and the like, inconspicuous, a material having as a transmitted light component, a color gamut which is a complementary color for the skin color to be adjusted or in proximity to that complementary color is compounded in a skin-color adjusting composition. When this composition is applied on the hyperchromic portion of the skin, the hyperchromic portion naturally becomes inconspicuous without deteriorating the transparent feel of the skin.

Also, in the colored titanium oxide coated mica is characterized that, as a skin-color adjusting composition, a fine particle of iron oxide having an average particle diameter of 60–150 nm is coated on the titanium oxide coated mica, so as not to be big the absorption of light by iron oxide on the surface and not to be weakened by the transmitted interference color.

35 Claims, 9 Drawing Sheets

5,690,916

1

SKIN-COLOR ADJUSTING METHOD, SKIN-COLOR ADJUSTING COMPOSITION AND COLORED TITANIUM OXIDE COATED MICA USED THEREFOR

FIELD OF THE INVENTION

The present invention relates to a method of adjusting a skin color, a composition used for adjusting the skin color, and a colored titanium oxide coated mica used therefor. More specifically, the present invention relates to skin-color adjusting method and composition by which a hyperchromic portion of the skin caused by nevus, angioma, red face, spots, freckles, and the like can become inconspicuous and a colored titanium oxide coated mica suitable for that composition, which has a transmitted light component with excellent dichroism and chroma.

BACKGROUND OF THE INVENTION

In the conventional cosmetic preparations exemplified by makeup cosmetic preparations, white pigments such as talc, titanium oxide, mica, kaolin, zinc oxide, and magnesium carbonate and color pigments such as iron oxide, carbon black, and lake pigment are appropriately compounded as cosmetic bases together with dyes, fats and oils, emulsifiers, fragrances, and the like to form cosmetic preparations such as face powder, solid face powder, emulsion-type foundation, water-dispersion type foundation, oil-dispersion type foundation, lipstick, and the like.

Recently, as japanese Unexamined Patent Publication No. 2-304015 which discloses a makeup cosmetic preparation for skin troubles in which powder having a high hiding ability such as aluminum is used, a commercial demand for cosmetic preparations which can cover abnormal hyperchromic portions of the skin has been increasing.

In general, these conventional cosmetic preparations for covering the abnormal hyperchromic portions of the skin use a base having a high hiding ability such as titanium dioxide, zinc white, or the like to cover an abnormal hyperchromic portion of the skin, while a pigment for adjusting the color of the compound on the skin to a preferred skin color is compounded therein.

However, it is a difficult for thus compounded cosmetic preparations to cover abnormal hyperchromic portions of the skin (e.g., spots, freckles, nevus, and angioma) in a natural manner.

Namely, since a base having a high hiding ability, thick application, or a cosmetic preparation having a large amount of pigments is used with respect to wide and abnormal hyperchromic portions of the skin caused by Ota's nevus, angioma, and the like, a natural skin color with a transparent feel cannot be obtained.

Namely, the skin not only reflects light on its surface but also acts as a semitransparent film with respect to the light. The light passes through several millimeters of the skin, while the appearance of the skin is determined by the light reflected on each skin layer. Accordingly, the skin exhibits a particular appearance with a transparent feel. However, when a large mount of a pigment having a high hiding ability is used, substantially whole the light is reflected on the pigment layer, thus yielding an unnatural appearance without any transparent feel.

SUMMARY OF THE INVENTION

In view of the foregoing circumstances, an object of the present invention is to provide a skin-color adjusting

2 method, skin-color adjusting composition, and colored titanium oxide coated mica used therefore, which is enough to cover an abnormal hyperchromic portion of the skin and never spoil the transparent feel.

To achieve this aim, by taking into account such a material as mica which has a filter effect by which a light component having a specific wavelength can pass therethrough, the inventors of the present invention found out that by using such a filter effect is adjustable an abnormal hyperchromic portion of the skin without spoiling the transparent feel. And the inventors found out a colored titanium oxide coated mica which has an excellent color adjusting effect and in which transmitted coherent light is not weakened by coloring agents, by coating a fine particle iron oxide on titanium oxide coated mica and complete the present invention.

To achieve this aim, in a skin-color adjusting method of the present invention comprising the steps of using a material having a coherent light component so as to make a hyperchromic portion of the skin inconspicuous due to an interference action. Further, it is preferable to make the hyperchromic portion inconspicuous by coating on the material whose wavelength of the transmitted interference color which is a complementary color for the color of the hyperchromic portion of the skin.

And in a skin-color adjusting composition of the present invention comprising the material having, as a transmitted light component, a color gamut which is a complementary color for the skin color to be adjusted or in proximity to the complementary color. FOr further, it is preferable to compound with an amount not less than 10% by weight with respect to the whole powder amount in said composition. It is preferably that said material is titanium oxide coated mica.

Namely, skin-color adjusting method or composition of the present invention comprising the material having, as a transmitted light component, a color gamut which is a complementary color for the skin color to be adjusted or in proximity to said complementary color so as to make a hyperchromic portion of the skin inconspicuous.

In the present invention, the material (referred to as "coherent material" in the following) used in the method in accordance with the present invention has, as an interference color, a complementary color for the hyperchromic portion of the skin. It is compounded so as to make the hyperchromic portion of the skin inconspicuous. In general, chromatic or achromatic transparent thin materials or thin layers of such materials coated on a carrier are used with their color tone, thickness, or layer thickness being adjusted to a predetermined value.

In lieu of using the hiding ability of the base for covering the abnormal hyperchromic portion of the skin, by taking into account that the coherent light component passing through a coherent material which has a filter effect for a light component having a specific wavelength, the inventors of the present invention have developed skin-color adjusting method and composition. The mechanism of their operations will be explained with reference to the drawings as follows.

In the first place, as shown in FIG. 1A, the skin 10 has a normal skin color portion 10a and a hyperchromic portion (blued portion here) 10b. When white light 12 impinges on the skin 10, the light reflected on the normal skin color portion 10a conceptually consists of a blue reflected light component 12a and a red reflected light component 12b which are balanced with each other such that a beautiful skin color is observed. In the light reflected on the hyperchromic portion 10b, on the other hand, the blue reflected light component 12a and the red reflected light component 12b are out of balance such that the amount of the blue reflected light component 12b is relatively much larger than that of the red reflected light component 12a, thus yielding a blue appearance.

In order to mask the hyperchromic portion 10b, as shown in FIG. 1B, a pigment layer 14 having a high hiding power has conventionally been applied on the skin 10. As a result, the whole light is reflected on the pigment layer 14 such that the color of the pigment layer 14 is directly observed as the color of the skin. However, since the pigment layer 14 having a high hiding power is not transparent to light, the transparent feel which is inherent in the natural skin cannot be obtained at all.

Therefore, a material having a low hiding power and a transmitted light component which is in a complementary relationship with the color tone of the abnormal hyperchromic portion of the skin is used in the present invention.

Namely, for example, as shown in FIG. 1C, a composition 18 in which titanium oxide coated mica 16 has been compounded is applied to the skin 10. The reflected coherent light component of titanium oxide coated mica 16 is a blue coherent light component 12a', whereas the transmitted coherent light component thereof is a red coherent light component 12b'. Namely, when white light 12 impinges on titanium oxide coated mica 16, the blue coherent light component 12a' is reflected thereon, while the transmitted red coherent light component 12b' reaches the skin 10. The transmitted red coherent light component 12b' is reflected on the normal skin color portion 10a as in the case of FIG. 1A. Though the transmitted red coherent light component 12b' impinges on the blue hyperchromic portion 10b in the same manner, the light reflected on the hyperchromic portion 10b does not substantially contain a blue component since little blue light component impinges thereon.

As a result, both the normal skin-color portion 10a and abnormal blue hyperchromic portion 10b can be observed as substantially the same color tone. Also, since the hiding power of the layer of the composition 18 itself is low, a considerable amount of light impinges on the skin 10 so that a natural transparent feel inherent in the skin itself can sufficiently be exhibited.

In the following, the operations of the composition in accordance with the present invention will be explained in more detail with reference to FIGS. 2A and 2B.

In the first place, a case where monochromatic light impinges on a material (thin film) having a transmitted coherent light component will be studied. As shown in FIG. 2A, when monochromatic light 2 is incident on a thin film 1, a part of the monochromatic light 2 incident on the thin film 1 is reflected on its first surface 1a as a first reflected light component 3a, while the rest of the light passes through the thin film and is reflected on its second surface 1b as a second reflected light component 3b. Then, both the first reflected light component 3a and the second reflected light component 3b are simultaneously caught by eyes. At this stage, however, a phase change occurring at the interface between two different media should be taken into account. Namely, when the light passing through a medium 5 having a refractive index n is reflected and refracted on its interface with respect to a medium (thin film 1) having a refractive index n', the incident light beam and the reflected light beam have the same phase difference at the point of incidence in the case of n>n', while they have a phase difference of π therebetween in the case of n<n'. This phase difference corresponds to a half-wavelength shift.

Accordingly, when incident on an optically non-dense medium from an optically dense medium and then reflected on their interface, a light beam is reflected with its bent wave form. On the other hand, when incident on an optically dense medium from an optically non-dense medium and then reflected on their interface, a light beam is reflected with a form in which a half wavelength is lost at the point of incidence. In the case of refraction, however, the refracted light bears no phase change regardless of n>n' or n<n'. Therefore, in practice, at places where the thickness of the thin film 1 corresponds to a value obtained when the wavelength of the light beam is multiplied by an integral number, these actions of the light beams used cancel each other, thus yielding a darker appearance. On the other hand, where the thickness of the thin film 1 corresponds to the half wavelength of the light or a value obtained when the half wavelength of the light is multiplied by an odd number, the actions of the light components intensify each other, thus yielding a brighter appearance.

Next, the transmitted coherent light component will be studied. As shown in FIG. 2B, when the monochromatic light 2 is incident on the thin film 1 of a transparent material, a part of the monochromatic light 2 incident on the first surface 1a of the thin layer passes through the thin film 1 and then is emitted from the second surface 1b as a first transmitted coherent light component 4a, while the rest of the light is reflected on the second surface 1b and then on the first surface 1a and, thereafter, emitted from the second surface 1b as a second transmitted coherent light component 4b. The actions of these transmitted coherent light components 4a, 4b intensify each other and thus yield a brighter appearance at places where the thickness of the thin film 1 corresponds to a value obtained when the wavelength of the used light is multiplied by an integral number, while they cancel each other and thus yield a darker appearance at places where the thickness of the thin film 1 corresponds to the half wavelength of the light or a value obtained when the half wavelength of the light is multiplied by an odd number.

In the foregoing, the relationship between the thickness of the thin film and the intensity of light has been discussed in the case where monochromatic light impinges on the thin film. When white light impinges on a thin film having a specific thickness, the wavelength of the light component to be intensified changes according to the thickness of the thin film. At a predetermined film thickness, when light components having a certain wavelength in the reflected coherent light look brighter due to their mutually intensified actions, their corresponding light components in the transmitted coherent light look darker due to their mutually cancelled actions according to the same principle. As a result, a transmitted interference color which is in complementary relationship with the light component having the predetermined wavelength in the reflected coherent light is obtained. As explained in the foregoing, the coherent material has a filter effect for a light component having a specific wavelength. Accordingly, a filter for a light component having a specific wavelength can be obtained when the thickness of the thin film made of such a material is controlled.

On the other hand, the hyperchromic portion of the skin is recognized when white light is incident on the skin and thereby a light component having a wavelength corresponding to the hyperchromic portion is diffusively reflected. Accordingly, in order to make the hyperchromic portion of the skin inconspicuous, white light excluding the light component having a wavelength corresponding to the hyperchromic portion of the skin may be made incident on the skin. For example, in cases where the hyperchromic portion of the skin looks like blue, a material whose transmitted coherent light includes little or no light component having a wavelength near 400–550 nm may be applied on the skin to naturally suppress the blue coloring from within the skin, thereby making the hyperchromic portion of the skin inconspicuous. As mentioned above, the wavelength of the transmitted coherent light component can be controlled arbitrarily by adjusting the thickness of the thin film. in the surface coherent light (reflected coherent light), on the other hand, a light component having a wavelength in complementary relationship with the transmitted interference color is intensified on the basis of the above-mentioned principle. Therefore, when the hyperchromic portion of the skin looks like blue, the surface interference color becomes blue. However, the interference color is oriented to the direction of incidence of light and strongly exhibited near the regular reflection region while hardly recognizable in other directions. Accordingly, applying of foundation or compounding of a coloring agent together with the coherent material may be used to modify the interference color.

Further, the present invention provides a skin-color adjusting method or composition for making a red hyperchromic portion of the skin inconspicuous characterized in that a material whose transmitted light has a maximum peak at a wavelength range of 400–550 nm (i.e., has a color of blue to green) is compounded with an amount not less than 10% by weight with respect to the whole powder amount in the composition. This method or composition is particularly useful for making a red hyperchromic portion of the skin such as angioma inconspicuous. When a titanium oxide coated mica is used as the material whose transmitted light has a maximum peak at a wavelength of 400–550 nm (i.e., has a color of blue to green), it corresponds to a material in which titanium dioxide having an optical film thickness of 190–270 nm or 405–500 nm is coated on mica.

Also, the material used for the skin-color adjusting method and composition for making a red hyperchromic portion of the skin inconspicuous has a hiding ability not more than 100 when determined by the following measuring method A and a red-covering power of at least not less than 8 when determined by the following measuring method B.

A: With a concentration of 80% by weight, the skin-color adjusting composition is mixed with a nitrocellulose vehicle. This mixture is applied, with a thickness of 30 μm, to a hiding- chart having white and black backgrounds. Then, the color difference ΔE between measured values in the white and black backgrounds is used to determine the hiding ability according to the following equation (1):

$$\text{hiding ability} = (1/\Delta E) \times 100 \tag{1}$$

B: With a concentration of 80% by weight, the skin-color adjusting composition is mixed with a nitrocellulose vehicle. This mixture is applied, with a thickness of 30 μm, to a red transparent PET film. Then, colorimetry is conducted with an incident light angle of 45° and a light-receiving angle of −15° and the red-covering power is determined by the following equation (2):

$$\text{red-covering power} = [(V-W)/V] \times 100 \tag{2}$$

wherein V is an integrated value of the reflectivity of the red transparent PET film at 600–730 nm without being coated with the skin-color adjusting composition and W is an integrated value of the reflectivity of the red transparent PET film at 600–730 nm when coated with the skin-color adjusting composition.

Preferably, the red-covering power is not less than 10.

Also, the present invention provides a skin-color adjusting method or composition for making a blue hyperchromic portion of the skin inconspicuous characterized in that a material whose transmitted light has a minimum peak at a wavelength range of 400–550 nm (i.e., has a color of yellow to red) is compounded to be applied on the skin. This method or composition is particularly useful for making a blue hyperchromic portion of the skin such as Ota's nevus inconspicuous. When a titanium oxide coated mica is used as the material whose transmitted light has a minimum peak at a wavelength of 400–550 nm (i.e., has a color of yellow to red), it corresponds to a material in which titanium dioxide having an optical film thickness of 290–380 nm or 530–660 nm is coated on mica.

The material used for the skin-color adjusting method and composition for making a blue hyperchromic portion of the skin inconspicuous has a hiding ability of not more than 100 when determined by the following measuring method A and a blue-covering power of at least not less than 40 when determined by the following measuring method C.

A: With a concentration of 80% by weight, the skin-color adjusting composition is mixed with a nitrocellulose vehicle. This mixture is applied, with a thickness of 30 μm, to a hiding-chart having white and black backgrounds. Then, the color difference ΔE between measured values in the white and black backgrounds is used to determine the hiding ability according to the following equation (1):

$$\text{hiding ability} = (1/\Delta E) \times 100 \tag{1}$$

C: With a concentration of 80% by weight, the skin-color adjusting composition is mixed with a nitrocellulose vehicle. This mixture is applied, with a thickness of 30 μm, to a blue transparent PET film. Then, colorimetry is conducted with an incident light angle of 45° and a light-receiving angle of −15° and the blue-covering power is determined by the following equation (3):

$$\text{blue-covering power} = [(X-Y)/X] \times 100 \tag{3}$$

wherein X is an integrated value of the reflectivity of the blue transparent PET film at 400–550 nm without being applied on the skin-color adjusting composition and Y is an integrated value of the reflectivity of the blue transparent PET film at 400–550 nm when applied on the skin-color adjusting composition.

Preferably, the blue-covering power is not less than 45.

When necessary, in the cosmetic preparation used for the method in accordance with the present invention, ingredients such as oils, surfactants, moisturizers, thickeners, sequestering agents, ultraviolet absorbents, antiseptics, antioxidants, fragrances, and various drugs which are generally used in cosmetic preparations may be compounded.

In the present invention, not less than 10% by weight or, preferably, not less than 25% by weight of the coherent material is compounded with respect to the whole powder amount in the composition. For example, mica coated with titanium dioxide, mica coated with zirconium oxide, mica coated with alumina, mica coated with iron oxide, plate-like titanium oxide, plate-like iron oxide, plate-like alumina, mica coated with silica, plate-like silica, coherent resin powder, mica coated with low-order titanium oxide, fish scale flake, and these materials coated with chromatic organic or inorganic coloring agents may be listed as the coherent material. Also, the above-mentioned materials may be coated with or complexed with other organic materials, metal oxides, metals, or clay minerals.

When titanium oxide coated mica is used as the coherent material and iron oxide or the like is compounded in the base, the interference action of the titanium oxide coated mica is remarkably weakened by absorption and scattering of light caused by iron oxide or the like. Therefore, there has conventionally been known a material called a dichroic pearl agent in which iron oxide or the like is directly coated on the titanium oxide coated mica to suppress the absorption and scattering of light caused by iron oxide or the like. However, since the particle diameter of iron oxide or the like in the dichroic pearl agent is as large as several hundred nm, its absorption of light becomes so high that the transmitted coherent light by titanium oxide coated mica is weakened, thereby making it difficult to sufficiently yield the aimed effects.

The colored titanium oxide coated mica of the present invention comprising a fine particle of iron oxide having an average particle meter of 60–150 nm coated on titanium oxide coated mica. Preferably, the ratio of titanium oxide coated mica (A) and iron oxide fine particle (B) is within the range of (A):(B)=(99.5:0.5)–(90:10).

Accordingly, in the present invention, a skin-color adjusting composition for making the hyperchromic portion of the skin inconspicuous which has a coherent material, a complementary color for the color of the skin to be adjusted and contains a colored titanium oxide coated mica in which a fine particle of iron oxide having an average particle diameter of 60–150 nm is coated on titanium oxide coated mica is preferable. The ratio of titanium oxide coated mica (A) and iron oxide fine particle (B) is preferably within the range of (A):(B)=(99.5:0.5)–(90:10) or, more preferably, within the range of (A):(B)=(99:1)–(97:3). The transmitted interference may become weak when the ratio of (A):(B) exceeds 90:10, whereas the dichroism may become weak when the ratio of (A):(B) is smaller than 99.5:0.5.

The average particle diameter of the iron oxide fine particle is 60–150 nm or, preferably, 80–120 nm. The coloring effect of iron oxide may become weak and the dichroism may be deteriorated when the average particle diameter is smaller than 60 nm, whereas the absorption of light by iron oxide may become strong and thereby the transmitted interference may be weakened when the average particle diameter is larger than 150 nm.

When the colored titanium oxide coated mica in accordance with the present invention is used as the coherent material for adjusting the skin color, since it is coated with the iron oxide free particle having a particle diameter as small as 60–150 nm, the absorption of light caused by iron oxide is so small that the transmitted coherent light is not weakened by coloring agents.

In the skin-color adjusting composition in accordance with the present invention, not less than 10% by weight or, preferably, not less than 15% by weight of the colored titanium oxide coated mica is compounded with respect to the whole powder amount in the composition.

Various methods may be used to make titanium oxide coated mica which is a matrix for the colored titanium oxide coated mica in accordance with the present invention.

While a vacuum deposition process may be used as such a method, as disclosed in Japanese Patent Publication No. 43-25644, a method comprising the steps of decomposing an inorganic salt of titanium such as titanyl sulfate or titanium tetrachloride in the presence of mica by a neutralization technique or a hydrolysis technique, depositing water-containing titanium oxide or titanium dioxide, and then firing it at a temperature of 500°–1000° C. or, preferably, of 700°–900° C. in the air is generally used. Mica to be used may be of any kind such as muscovite, biotite, phlogopite, or synthetic mica. While not particularly limited, it is preferable for mica to have a particle diameter in the order of 1–50 μm and a particle form as flat as possible when used as a cosmetic pigment or general industrial pigment, since a beautiful interference color is likely to be exhibited.

As an example of a method for making the colored titanium oxide coated mica in accordance with the present invention, the following method may be used. Into an aqueous solution of an inorganic or organic iron compound such as ferrous chloride, ferric chloride, ferrous sulfate, ferric sulfate, ferrous nitrate, ferric nitrate, ferrous oxalate, ammonium ferric oxalate, ammonium ferric sulfate, ferric phosphate, ferric citrate, ferrous lactate, or iron fumarate, titanium oxide coated mica synthesized by the above-mentioned method is added. Then, the resulting aqueous solution of the iron compound in which titanium oxide coated mica has been dispersed is adjusted to a pH of 5.6–7.0 or, preferably, of 6.0–6.5 by such an alkali as caustic soda, caustic potash, or aqueous ammonia to neutralize and decompose a part of the iron compound so as to deposit ultra fine particles of water-containing iron oxide on the surface of titanium oxide coated mica particles. After thus formed aqueous solution of the iron compound, in which titanium oxide coated mica coated with the ultra fine particles of water-containing iron oxide has been dispersed, is heated to a temperature of 50°–100° C. or, preferably, of not lower than 80° C., the pH thereof is maintained at 8.0–9.5 by addition of an aqueous solution of such an alkali as caustic soda, caustic potash, or aqueous ammonia so as to completely neutralize and decompose the iron compound. Then, it is fired at a temperature of not lower than 150° C. or, preferably, of not lower than 400° C. to make a titanium oxide coated mica coated with fine particles of iron oxide whose nucleus is the ultra fine particle of iron oxide previously deposited on the surface of the titanium oxide coated mica particle.

Alternatively, urea may be added to the aqueous solution of the iron compound, in which the above-mentioned titanium oxide coated mica coated with the ultra fine particles of water-containing iron oxide has been dispersed, with an amount not lower than the equivalent needed for the neutralizing decomposition of the iron compound. Then, the resulting mixture may be heated to and maintained at a temperature of 50°–100° C. or, preferably, not lower than 80° C., while being stirred, so as to completely neutralize and decompose the iron compound. Thereafter, it may be fired at a temperate of not lower than 150° C. or, preferably, of not lower than 400° C. to make a titanium oxide coated mica coated with fine particles of iron oxide whose nucleus is the ultra fine particle of iron oxide previously deposited on the surface of the titanium oxide coated mica particle. Alternatively, urea may be added together with the iron compound before the reaction.

The colored titanium oxide coated mica in accordance with the present invention may be used as a pigment for cosmetic preparations utilizing its dichroism. Preferably, not less than 10% by weight of the colored titanium oxide coated mica is compounded with respect to the whole powder amount in a cosmetic preparation.

Further, when having a skin-color adjusting composition for making a hyperchromic portion of the skin inconspicuous by using the colored titanium oxide coated mica of the present invention, it is preferable to compound the colored titanium oxide coated mica which has a interference color which is a complementary color for the skin color to be adjusted, and is coated on a fine particle of iron oxide having an average particle diameter of 60–150 nm coated on titanium oxide coated Also, when using for a skin-color adjusting composition for making a red hyperchromic portion of the skin inconspicuous, it is preferable to the composition comprising a colored titanium oxide coated mica, the titanium material composed of titanium dioxine having an optical film thickness of 190–270 nm or 405–500 nm coated on mica and a fine particle of iron oxide having an average particle diameter of 60–150 nm coated thereon.

Alternatively, when using for a skin-color adjusting composition for making a blue hyperchromic portion of the skin inconspicuous, it is preferable to the composition comprising a colored titanium oxide coated mica, the titanium material composed titanium dioxine having an optical film thickness of 290–380 nm or 530–660 nm coated on mica and a fine particle of iron oxide having an average particle diameter of 60–150 nm coated thereon.

Powder ingredients which may be compounded in the composition of the present invention include inorganic powder such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc myristate, calcium palmitate, and aluminum stearate), and boron nitride; organic powder such as polyamide resin powder (nylon powder), polyethylene powder, methyl polymethacrylate powder, polystyrene powder, copolymer powder of styrene and acrylic acid, benzoguanamine resin powder, poly(ethylene tetrafluoride) powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide, carbon black, and low-order titanium oxide; inorganic violet pigments such as mango violet and cobalt violet; inorganic green pigments such as chromium oxide, chromium hydroxide, and cobalt titanate; inorganic blue pigments such as ultramarine blue and iron blue; pearl pigments such as titanium oxide coated talc, color titanium oxide coated mica, titanium oxide coated bismuth oxychloride, color titanium oxide coated mica, bismuth oxychloride, and fish scale flake; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; organic pigments based on lakes of zirconium, barium and aluminum or the like such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1; and natural coloring matters such as chlorophyll and β-carotene. These ingredients may be used separately as well as in combination of two or more. The ingredients are not restricted to those listed above as long as they can be applied to general cosmetics.

When necessary, in the cosmetic preparation preferable for the operation mode in the present invention, ingredients such as oils, surfactants, moisturizers, thickeners, sequestering agents, ultraviolet absorbents, antiseptics, anti-oxidants, fragrances, and various drugs which are generally used in cosmetic preparations may be compounded.

Those chemicals or cosmetics which is permissible as a base mentioned following.

Oils may be material oils which are applicable to cosmetics. For example, hydrocarbons, esters, glycerides, lower alcohols, higher alcohols, polyhydric alcohols, higher fatty adds, and organopolysiloxane fluids such as liquid paraffin, squalane, vaseline, polyisobutyrene, microcrystalline wax, isopropyl myristate, myristyl octyl dodecanol, di-(2-ethylhexyl) succinate, diisooctanoic acid neopentyl glycol, glycerine monostearate, isostearic add triglyceride, coconut-oil fatty acid triglyceride, castor oil, ethanol, octyl dodecanol, hexadecyl alcohol, cetyl alcohol, oleyl alcohol, stearyl alcohol, polyethylene glycol, lauric acid, palmitic acid, oleic acid, stearic acid, isostearic acid, lanolin, beeswax, and olive oil may be used.

The skin-color adjusting composition in accordance with the present invention contains the above-mentioned colored titanium oxide coated mica and can be used mainly as a makeup cosmetic preparation and, among others, as a base-making preparation. When used as a makeup cosmetic preparation, depending on its kind and use, the composition may not only consist of the colored titanium oxide coated mica alone but also include at least one member selected from the group consisting of various powder materials, oils, and water in addition to the titanium oxide coated mica. The powder materials and oils which may be compounded in addition to the colored titanium oxide coated mica are similar to the case of the conventional cosmetic preparation. Also, when necessary, in the composition in accordance with the present invention, ingredients such as oils, surfactants, moisturizers, thickeners, metal-ion blocking agents, ultraviolet absorbents, antiseptics, anti-oxidants, fragrances, and various drugs which are generally used in cosmetic preparations may be compounded.

EXAMPLES

Figure 1A:
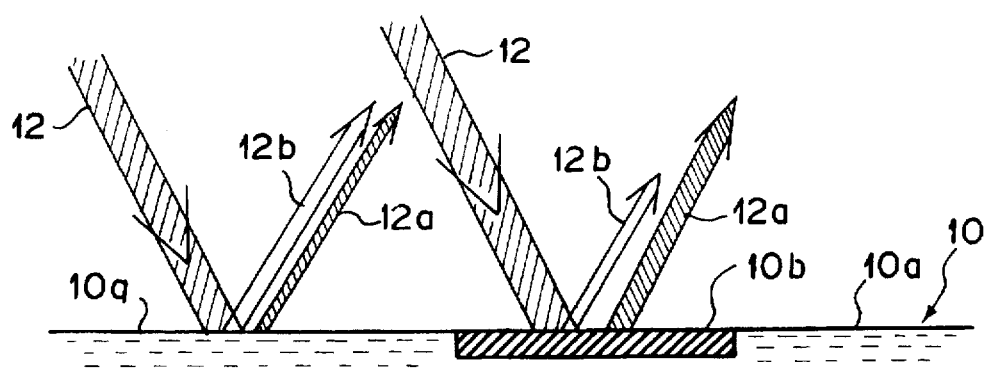
FIGS. 1A–1C are explanatory views comparing the interference actions at hyperchromic and normal skin-color portions in the present invention with those of the prior art.
Figure 1B:
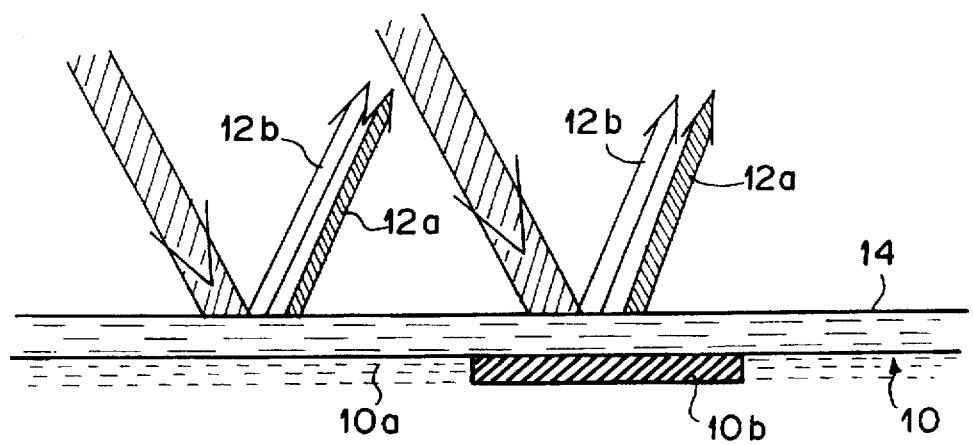
Figure 1C:
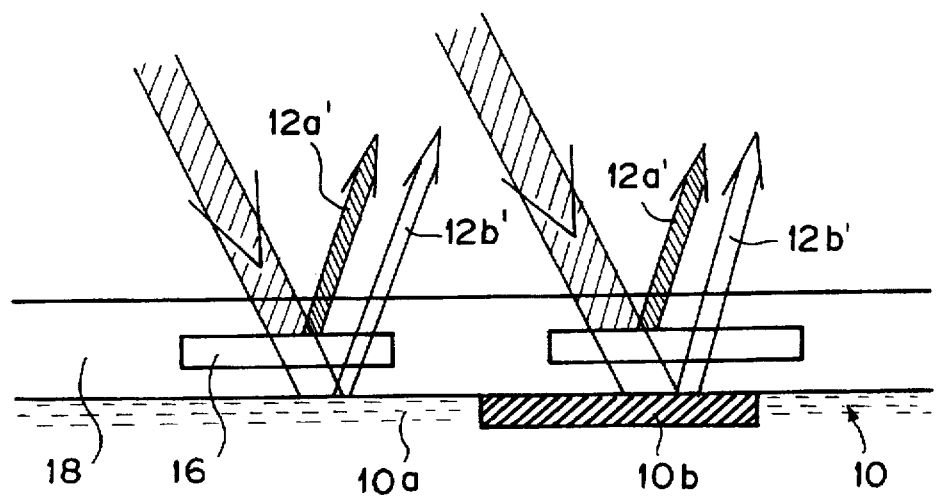
Figure 2A:
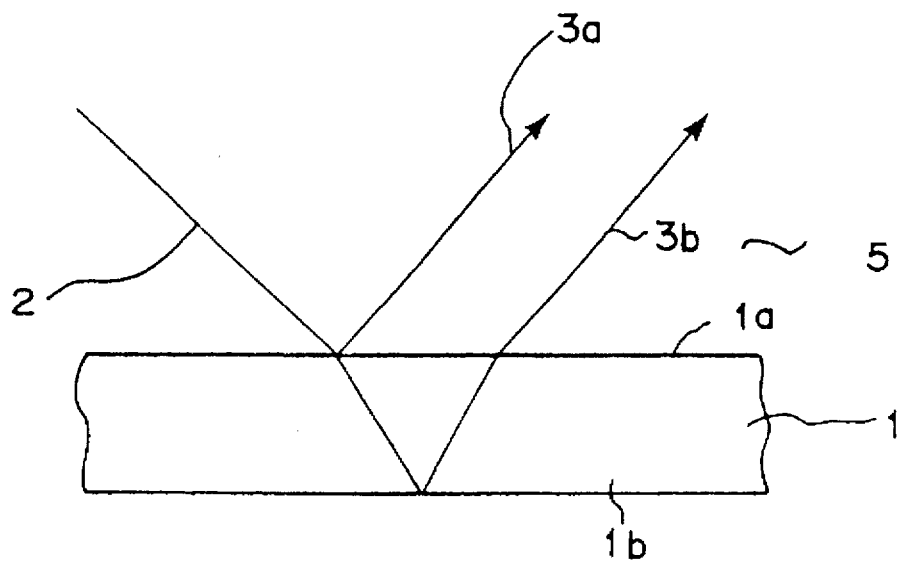
FIGS. 2A and 2B are explanatory views explaining the actions of a coherent material.
Figure 2B:
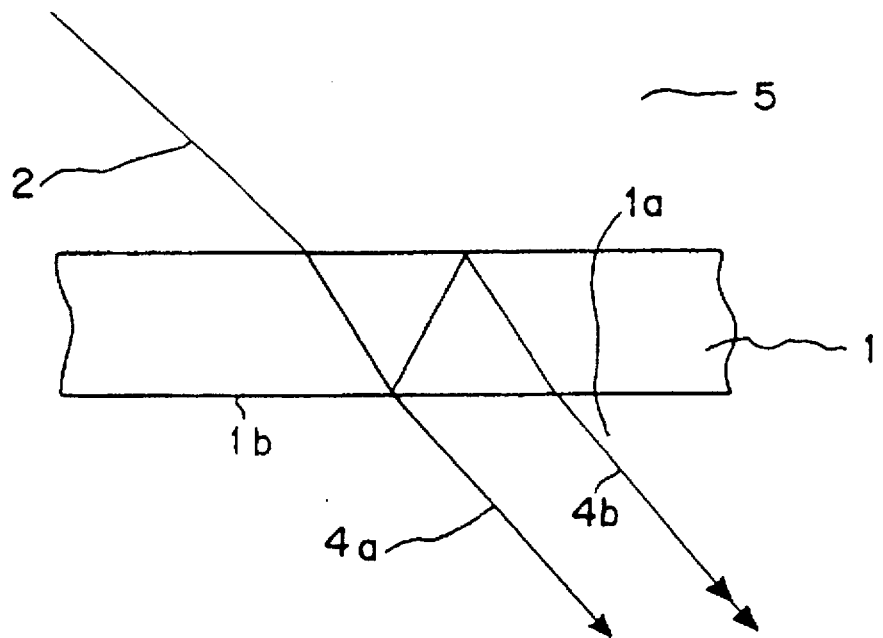

In the following, the skin-color adjusting method, colored titanium oxide coated mica, and color-adjusting composition in which that material is compounded in accordance with the present invention will be explained. However, the present invention is not limited to these examples. All the compounding ratios in the following are % by weight.

In the first place, the inventors took notice of the relationship between the hiding ability and the natural appearance of the skin. Namely, compact foundation samples were made with the basic compositions shown in TABLE 1. Then, their hiding power values were determined by the aforesaid method. Also, they were applied to a skin having a normal skin-color and then the appearance of the skin was observed. The results are shown in TABLE 1.

TABLE 1

| | | Sample | | | | |
|---|---|---|---|---|---|---|
| | | 1 | 2 | 3 | 4 | 5 |
| (1) | Carnauba wax | 1.0 | 1.0 | 1.0 | 1.0 | 1.0 |
| (2) | Microcrystalline wax | 5.0 | 5.0 | 5.0 | 5.0 | 5.0 |
| (3) | Decamethyl cyclo-pentasiloxane | 8.5 | 8.5 | 8.5 | 8.5 | 8.5 |
| (4) | Squalane | 21.0 | 21.0 | 21.0 | 21.0 | 21.0 |
| (5) | Cetyl-2-etylhexanoate | 15.0 | 15.0 | 15.0 | 15.0 | 15.0 |
| (6) | Sorbitan dioleate | 1.5 | 1.5 | 1.5 | 1.5 | 1.5 |
| (7) | Titanium dioxide | 5.0 | 10.0 | 15.0 | — | — |
| (8) | Iron oxide pigment | 3.0 | 3.0 | 3.0 | 3.0 | 3.0 |
| (9) | Aluminum powder | — | — | — | 8.0 | 15.0 |
| (10) | Mica | 31.0 | 21.0 | 16.0 | 23.0 | 16.0 |
| (11) | Globular nylon | 4.0 | 4.0 | 4.0 | 4.0 | 4.0 |
| (12) | Fragrance | proper amount | proper amount | proper amount | proper amount | proper amount |
| | Hiding ability | 28 | 66 | 100 | 500 | 1,000 |
| | Naturalness | ☉ | ☉ | ○ | △ | X |

As clearly shown by TABLE 1, the hiding ability of the composition and the naturalness observed when actually applied to the skin are mutually related to each other. Namely, powdery feel is observed from the skin when a composition whose hiding ability exceeds 500 is applied thereto. In order to maintain the natural appearance of the skin, it is necessary for the hiding ability to be not higher than about 100.

However, compositions whose hiding ability is not higher than 100, such as Sample Nos. 1 and 2, can hardly make abnormal hyperchromic portions on the skin inconspicuous.

Accordingly, in order to adjust the skin color of the abnormal hyperchromic portions on the skin without increasing the hiding ability, the inventors studied the applicability of coherent materials.

MANUFACTURING EXAMPLE 1

In the first place, as an example of the coherent materials preferably used in the present invention, an example for making a titanium oxide coated mica coated with a fine particle of iron oxide will be explained.

To 500 parts of ion-exchanged water, 50 parts of mica was added and uniformly dispersed therein by sufficient stirring. To thus obtained dispersion liquid, 312.5 parts of titanyl sulfate aqueous solution having a concentration of 40% by weight was added. The resulting mixture was heated while being stirred and then boiled for 6 hours. After being left for cooling, the mixture was subjected to filtering. The filtered-out product was washed with water and, then fired at 900° C. to yield 100 parts of a mica material coated with titanium dioxide (titanium oxide coated mica) having an interference color of blue.

On the other hand, 53.6 parts of ammonium ferric oxalate and 22.5 parts of urea were dissolved in 2,000 parts of ion-exchanged water. The pH of the resulting aqueous solution was adjusted to 5.8 by 0.1M caustic soda aqueous solution. Then, 100 parts of titanium oxide coated mica which had been made as mentioned above was added thereto and uniformly dispersed therein by sufficient stirring.

Thereafter, this titanium oxide coated mica dispersion liquid whose pH had been adjusted to 5.8 was heated while being stirred and then boiled for 6 hours. After being left for cooling, it was subjected to filtering. The filtered-out product was washed with water and then fired at 400° C. to yield 103 parts of a titanium oxide coated mica coated with a fine particle of iron oxide having skin-color appearance, vivid blue reflected interference color, and vivid yellow transmitted interference color.

Figure 3:
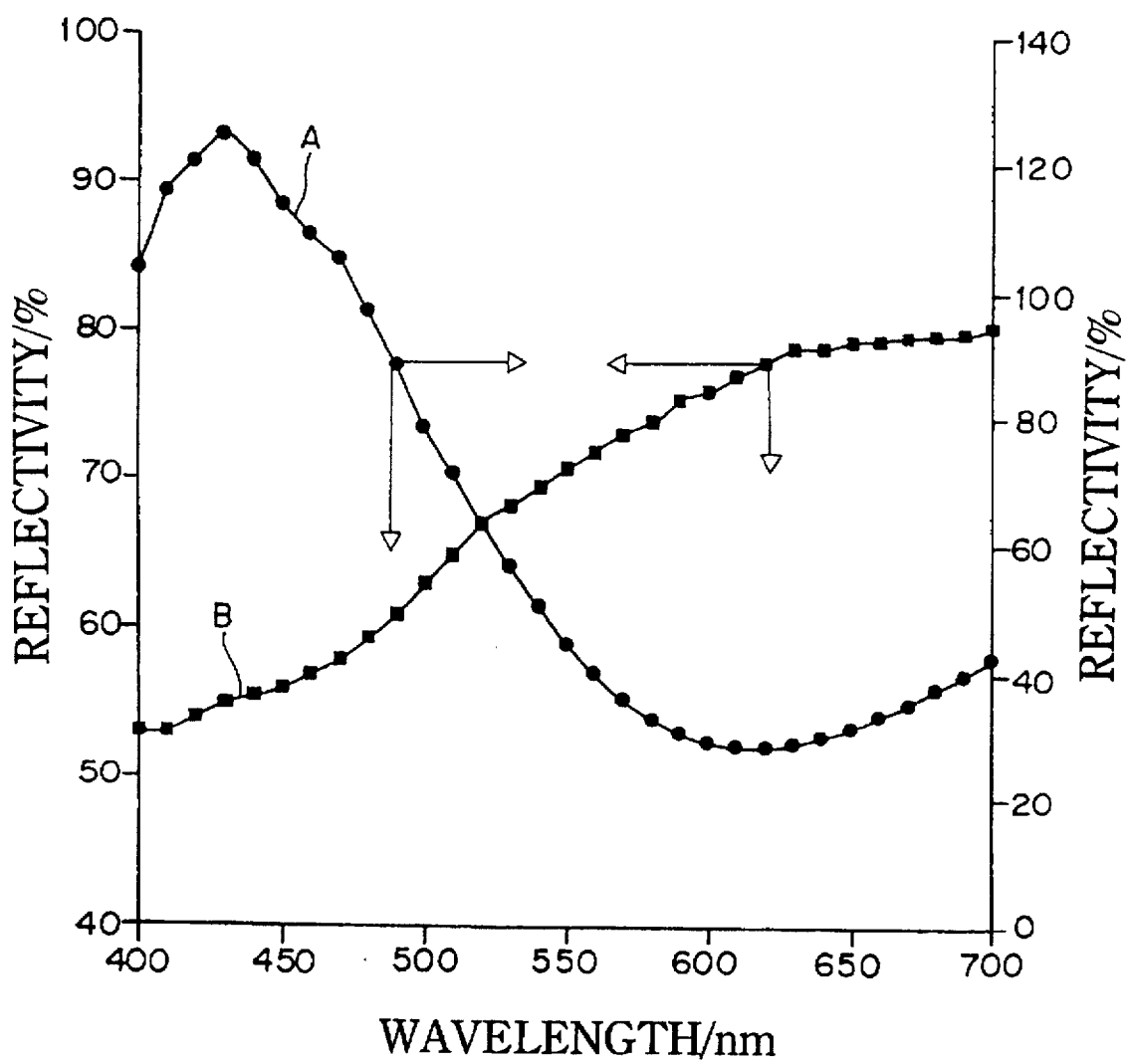
FIG. 3 is a characteristic chart showing the wavelength-dependence of reflectivity of reflected light and transmitted light in a titanium oxide coated mica coated with a fine particle of iron oxide in accordance with the present invention.
Figure 4:
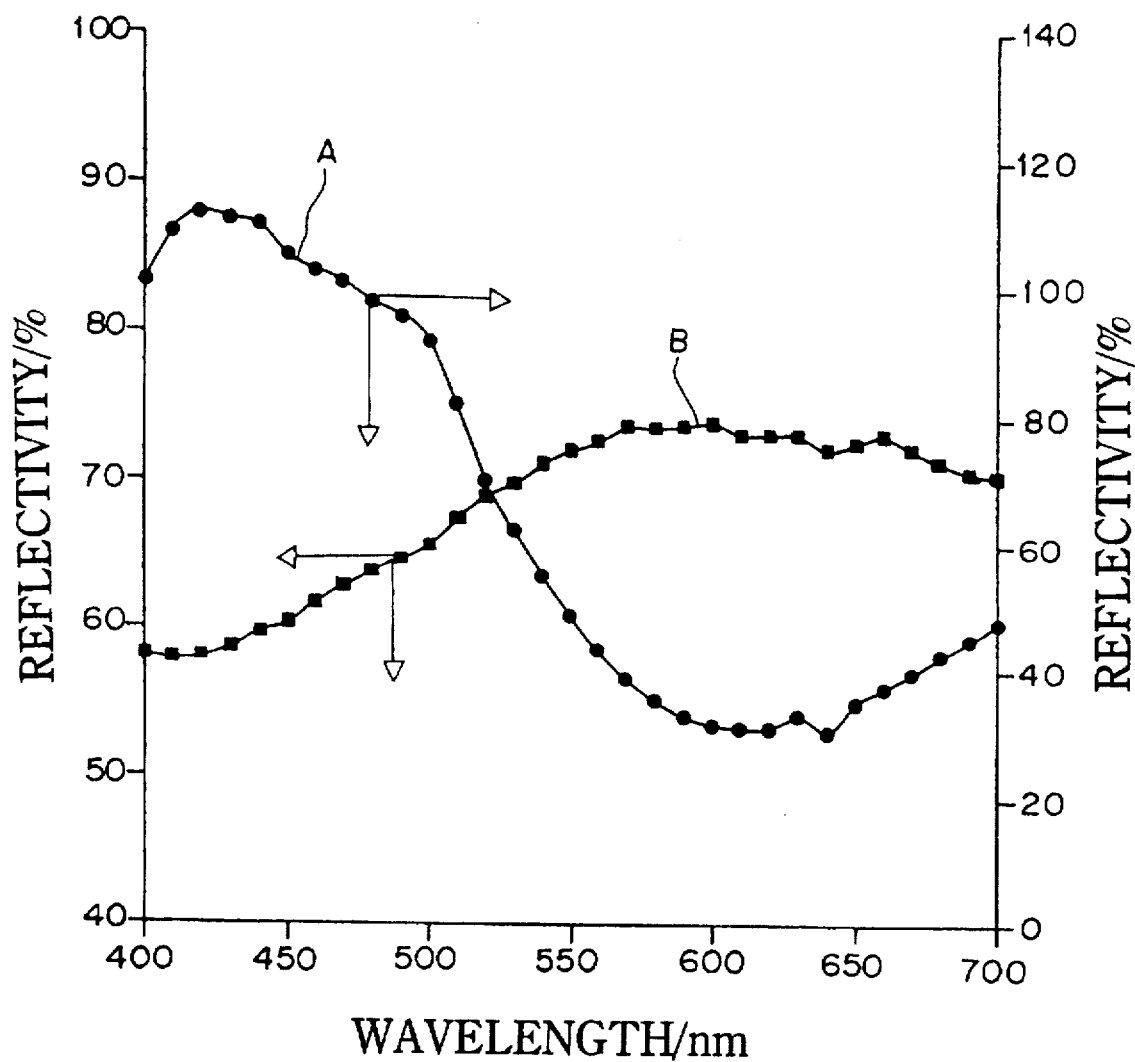
FIG. 4 is a characteristic chart showing the wavelength-dependence of reflectivity of reflected light and transmitted light in a conventional titanium oxide coated mica coated with iron oxide.

FIG. 3 shows the relationship between wavelength (nm) and reflectivity (%) in the reflected coherent light (indicated as "A" in the chart) and transmitted coherent light (indicated as "B" in the chart). The reflected coherent light was measured by a goniospectrophotometer GCMS-3 manufactured by Murakami Color Lab., while the transmitted coherent light was measured by a chromatoscanner manufactured by Shimadzu Seisakusho. For comparison, FIG. 4 shows the results of similar measurement conducted for a commercially-available titanium oxide coated micacoated with iron oxide (Duocrome YB manufactured by Mearl Corp.) as in the case of FIG. 3 When FIGS. 3 and 4 are compared with each other, it is recognized that the spectral reflectance curves of both transmitted coherent light and reflected coherent light in the material of the present invention are higher and more sharp than those of the conventional material. Also, the minimum reflection and maximum reflection are found to exist in a nearly single wavelength light component. Accordingly, it is understood that the transmitted coherent light and reflected coherent light in the material of the present invention are stronger and have higher chroma values than those of the conventional material.

Figure 5:
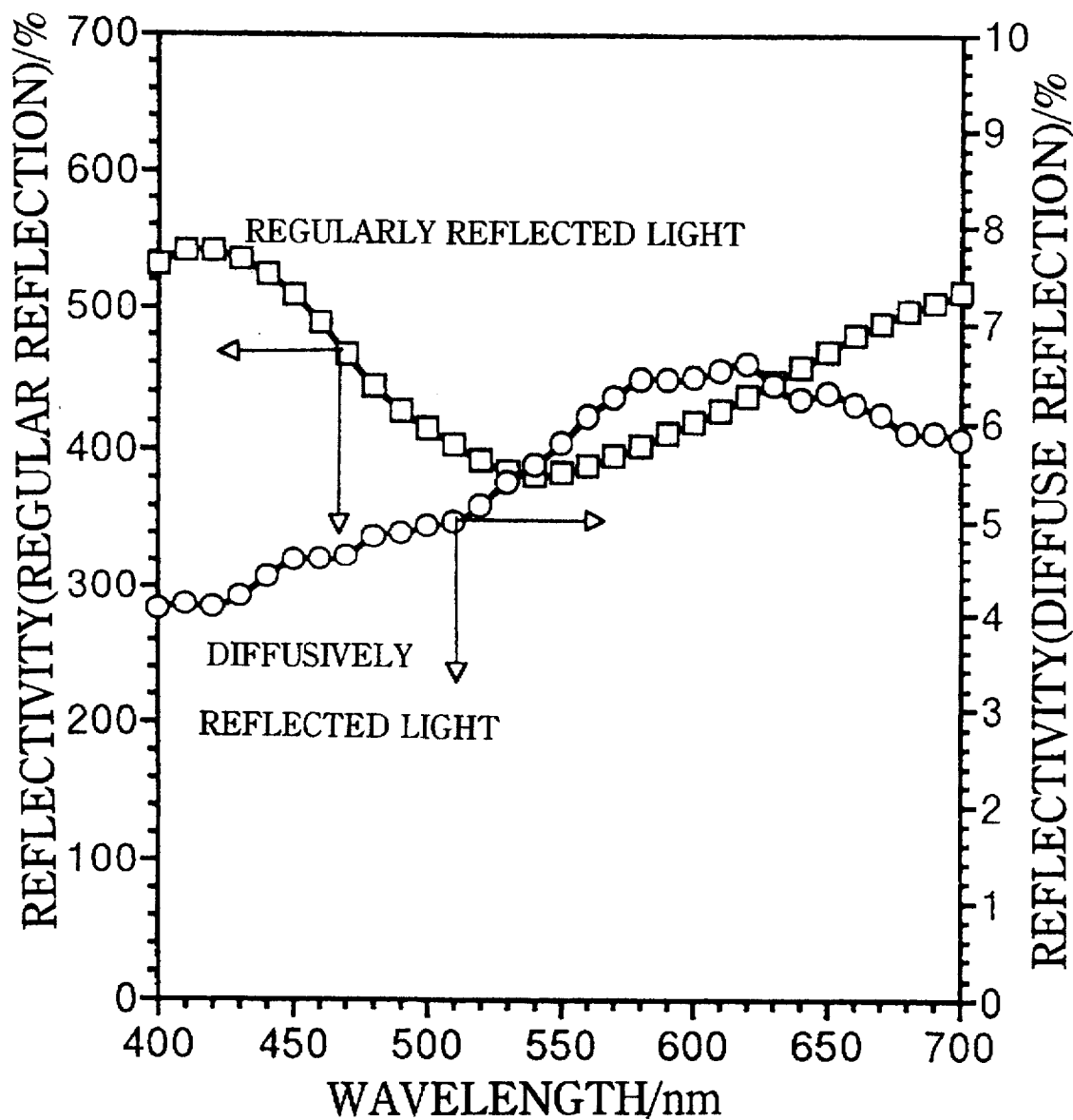
FIG. 5 is a characteristic chart showing the wavelength-dependence of reflectivity of regularly reflected light and diffusively reflected light in a titanium oxide coated mica coated with a fine particle of iron oxide in accordance with the present invention.

FIG. 5 shows the relationship between the wavelength of regularly reflected light and diffusively reflected light and their reflectivity in thus obtained titanium oxide coated mica coated with the iron oxide fine particle. The goniospectrophotometer GCMS-3 manufactured by Murakami Color Lab. was used to determine this relationship. The conditions were an incident angle of −70°, a diffused reflection angle of −50°, a sample thickness of 15 μm, and a transparent PET film thickness of 10 μm. For comparison, FIG. 6 shows the results of similar measurement conducted for a commercially-available titanium oxide coated mica coated with iron oxide (Duocrome YB manufactured by Mearl Corp.) having blue reflected interference color as in the case of FIG. 6.

Figure 6:
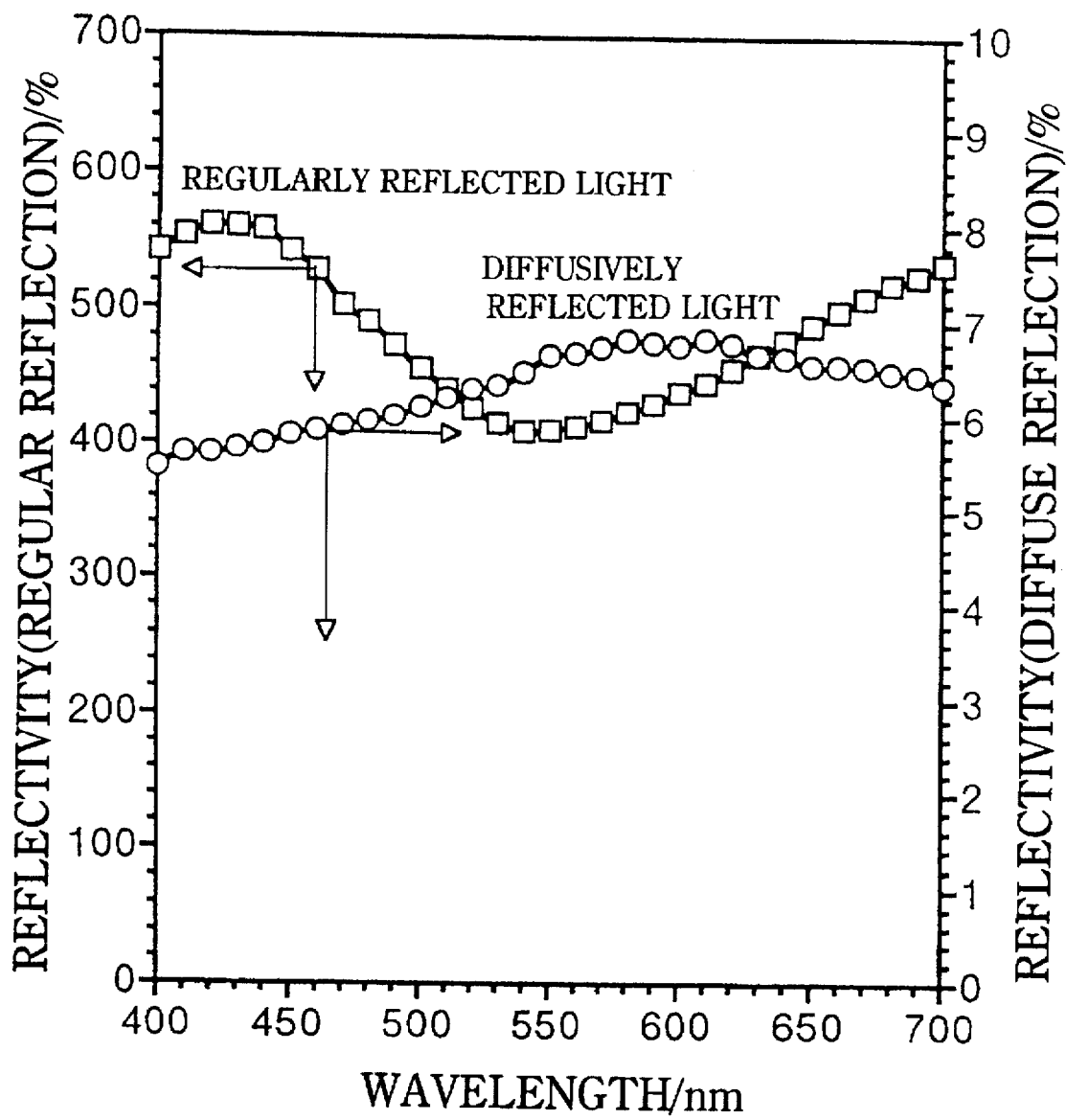
FIG. 6 is a characteristic chart showing the wavelength-dependence of reflectivity of regularly reflected light and diffusively reflected light in a conventional titanium oxide coated mica coated with iron oxide.
Figure 7:
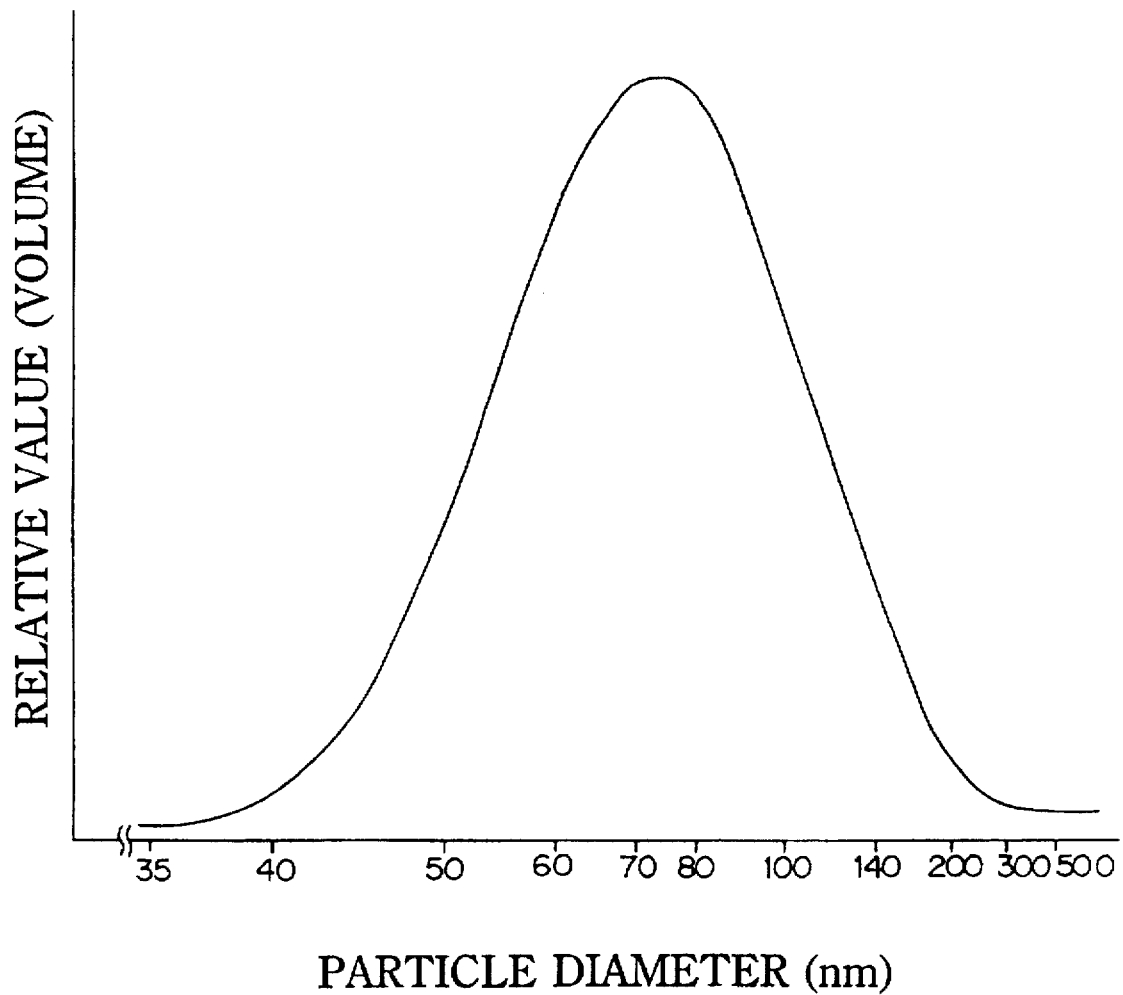
FIG. 7 is a chart showing the particle-size distribution in a titanium oxide coated mica coated with a fine particle of iron oxide in accordance with the present invention.

When FIGS. 5 and 6 are compared with each other, it is recognized that the spectral reflectance curves of both regularly reflected light and diffusively reflected light in the material of the present invention have a greater difference in reflectivity and are more sharp than those of the conventional material. Accordingly, it is understood that, as compared with the conventional material, the material of the present invention is a colored titanium oxide coated mica (color pearl pigment) having stronger regularly reflected light and diffusively reflected light as well as a high chroma value and an excellent dichroism.

MANUFACTURING EXAMPLE 2

In 2,000 parts of ion-exchanged water, 53.6 parts of ammonium ferric oxalate and 22.5 parts of urea were dissolved. The pH of the resulting aqueous solution was adjusted to 6.2 by 0.1M caustic soda aqueous solution. Then, 100 parts of a red interference titanium oxide coated mica (Timilon Super Red) manufactured by German Merck Corp. was added thereto and uniformly dispersed therein by sufficient stirring.

Thereafter, this titanium oxide coated mica dispersion was heated, while being stirred, and boiled for 6 hours. After being left for cooling, it was subjected to filtering. The filtered-out product was washed with water and then fired at 400° C. to yield 102 parts of a titanium oxide coated mica coated with a fine particle of iron oxide having skin-color appearance, vivid red reflected interference color, and vivid green transmitted interference color.

Separately, in order to study the particle size of the iron oxide coated on thus obtained red-interference titanium oxide coated mica coated with the iron oxide fine particle, iron oxide was synthesized under the same conditions as those of MANUFACTURING EXAMPLE 1 except that no titanium oxide coated mica was added thereto.

When the particle size of thus obtained iron oxide was measured by a laser diffraction type particle-size analyzer NICOMP 270 manufactured by Hiac/Royco Corp., a particle size distribution normally distributed in 35–300 nm with an average particle diameter of 71 nm was found.

Next, Examples 1–4 of the present invention in which a commercially-available mica compound compounded and Examples 5 and 6 in which the colored titanium oxide coated mica obtained by the foregoing MANUFACTURING EXAMPLES were compounded will be shown with reference to their comparative examples.

Examples 1 and 2 and Comparative Examples 1–3

Oily compact foundation samples for adjusting blue hyperchromic portions having compositions shown in TABLE 2 were made in the following method and their blue-covering power and hiding ability values were determined. These results are also shown in TABLE 2.

(Manufacturing Method)

After ingredients (3)–(6) were heated and dissolved, ingredients (7)–(14) were added thereto and dispersed therein in a dispersion mill. The resulting mixture was processed in a TK mill manufactured by Tokushu Kika and heated to 85° C. Then, ingredients (1) and (2), which had been heated, melted, and mixed together at 90° C. beforehand, as well as ingredient (15) were added thereto. After being deaerated, the mixture was charged into a predetermined mid-size plate and left for cooling to yield oily compact foundation samples for adjusting blue hyperchromic portions.

TABLE 2

| | | Example | | Comparative Example | | |
|---|---|---|---|---|---|---|
| Compounding formula | | 1 | 2 | 1 | 2 | 3 |
| (1) | Carnauba wax | 1.0 | 1.0 | 1.0 | 1.0 | 1.0 |
| (2) | Microcrystalline wax | 5.0 | 5.0 | 5.0 | 5.0 | 5.0 |
| (3) | Decamethyl cyclopentasiloxane | 8.5 | 8.5 | 8.5 | 8.5 | 8.5 |
| (4) | Squalane | 21.0 | 21.0 | 21.0 | 21.0 | 21.0 |
| (5) | Cetyl-2-ethylhexanoate | 15.0 | 15.0 | 15.0 | 15.0 | 15.0 |
| (6) | Sorbitan dioleate | 1.5 | 1.5 | 1.5 | 1.5 | 1.5 |
| (7) | Titanium oxide coated mica (blue interference color)[*1] | — | 20.0 | — | — | — |
| (8) | Titanium oxide coated mica (red interference color)[*2] | — | — | — | — | 20.0 |
| (9) | $Fe_2O_3$-coated mica[*3] | 20.0 | — | — | — | — |
| (10) | Titanium dioxide | 10.0 | 10.0 | 30.0 | — | 10.0 |
| (11) | Aluminum powder | — | — | — | 30.0 | — |
| (12) | Iron oxide pigment | 3.0 | 3.0 | 3.0 | 3.0 | 3.0 |
| (13) | Mica | 11.0 | 11.0 | 11.0 | 11.0 | 11.0 |
| (14) | Globular nylon | 4.0 | 4.0 | 4.0 | 4.0 | 4.0 |
| (15) | Fragrance | proper amount | proper amount | proper amount | proper amount | proper amount |
| | Blue-covering power | 50 | 60 | 32 | 69 | 8.6 |
| | Hiding ability | 12 | 7 | 484 | 2,852 | 13 |

[*1]: $TiO_2$-coated mica
[Flamenco Blue manufactured by Mearl Corp. with $TiO_2$/mica = (43–49)/(51–57), optical film thickness of $TiO_2$ at about 310 nm, and transmitted light of yellow to red]
[*2]: $TiO_2$-coated mica
[Flamenco Red manufactured by Mearl Corp. with $TiO_2$/mica = (37–43)/(57–63), optical film thickness of $TiO_2$ at about 250 nm, and transmitted light of blue to green]
[*3]: 34.0% $Fe_2O_3$-coated mica (with transmitted light of yellow to red)

Next, the covering effect, transparent feel, and finishing naturalness of thus obtained oily compact foundation samples for adjusting blue hyperchromic portions were evaluated. Namely, the samples were applied to 10 people having a hyperchromic portion of a heavy blue mark (Ota's nevus or the like), a third party observed and judged the results with five steps of 5 (effective or natural) to 1 (ineffective or unnatural, and then an average of thus evaluated values for each evaluation item was obtained.

Further, the skin color (in the normal and hyperchromic portions) was measured by a Minolta colorimeter CM-1000 before and after the application to determine the color difference therebetween. Then, an average of thus measured color differences was calculated for each item.

These results are shown in TABLE 3.

TABLE 3

| | Example | | Comparative Example | | |
|---|---|---|---|---|---|
| | 1 | 2 | 1 | 2 | 3 |
| Covering effect (Skin-color adjusting effect) | 4.3 | 4.5 | 4.5 | 4.8 | 2.2 |
| Transparent feel | 3.2 | 3.9 | 1.9 | 2.5 | 3.5 |
| Finishing naturalness | 3.9 | 4.1 | 2.5 | 1.2 | 2.5 |
| Color difference (Δ E) between normal naked skin and hyperchromic naked skin | 18.1 | 18.1 | 18.1 | 18.1 | 18.1 |

TABLE 3-continued

|  | Example | | Comparative Example | | |
|---|---|---|---|---|---|
|  | 1 | 2 | 1 | 2 | 3 |
| Color difference (Δ E) between normal skin and hyperchromic skin after application | 2.6 | 1.2 | 3.8 | 6.4 | 7.0 |

As clearly shown by TABLE 3, the foundation samples of Examples 1 and 2 in which powder having yellow to red transmitted light had been compounded in accordance with the present invention not only were excellent in covering blue hyperchromic portions of Ota's nevus or the like (i.e. in skin-color adjusting effect) but also yielded transparent feel and natural finishing. In particular, Example 2 which used a titanium oxide coated mica having yellow to red transmitted coherent light yielded excellent finishing feel which had not conventionally been experienced. Also, when a commercially-available powdery foundation was applied after the application of these adjusting foundations, the gloss of titanium oxide coated mica changed into a natural transparent feel so as to yield a finishing feel which was comparable to the normal portion.

On the other hand, Comparative Example 1, in which a large amount of conventionally-used titanium dioxide had been compounded, yielded a powdery finish without transparent feel, while exhibiting a covering effect. Also, though Comparative Example 2, in which aluminum powder had been compounded, showed an excellent hiding characteristic, it yielded an unnatural glossy feel in finishing and a roughness was felt when in use. Further, interestingly, Comparative Example 3, which used a titanium oxide coated mica having yellow to red reflected light which was in complementary color relationship with Example 2, hardly showed the covering effect, though exhibiting a transparent feel. Therefore, it was unfavorable as an adjusting foundation.

Examples 3 and 4 and Comparative Examples 4–6

Stick foundation samples for adjusting red hyperchromic portions having compositions shown in TABLE 4 were made in the following method and their red-covering power and hiding ability values were determined. These results are also shown in TABLE 4.

(Manufacturing Method)

After ingredients (3)–(6) were heated and dissolved, ingredients (7)–(14) were added thereto and dispersed therein in a dispersion mill. The resulting mixture was processed in a TK mill manufactured by Tokushu Kika and heated to 85° C. Then, ingredients (1) and (2), which had been heated, melted, and mixed together at 90° C. beforehand, as well as ingredient (15) were added thereto. After being deaerated, the mixture was charged into a predetermined stick container and then left for cooling to yield the oily stick foundation samples for adjusting red hyperchromic portions.

TABLE 4

|  |  | Example | | Comparative Example | | |
|---|---|---|---|---|---|---|
| Compounding formula | | 3 | 4 | 4 | 5 | 6 |
| (1) | Carnauba wax | 1.0 | 1.0 | 1.0 | 1.0 | 1.0 |
| (2) | Solid paraffin wax | 6.0 | 6.0 | 6.0 | 6.0 | 6.0 |

TABLE 4-continued

|  |  | Example | | Comparative Example | | |
|---|---|---|---|---|---|---|
| Compounding formula | | 3 | 4 | 4 | 5 | 6 |
| (3) | Dimethylsilicone | 7.5 | 7.5 | 7.5 | 7.5 | 7.5 |
| (4) | Liquid paraffin | 15.0 | 15.0 | 21.0 | 21.0 | 21.0 |
| (5) | Glyceryl monoisostearate | 20.5 | 20.5 | 20.5 | 20.5 | 20.5 |
| (6) | Sorbitan diisostearate | 2.0 | 2.0 | 2.0 | 2.0 | 2.0 |
| (7) | Hydrophobically-processed titanium oxide coated mica (red interference color)[*4] | — | 12.0 | — | — | — |
| (8) | Hydrophobically-processed titanium oxide coated mica (blue interference color)[*5] | — | — | — | — | 12.0 |
| (9) | Fe$_2$O$_3$-coated mica[*6] | 12.0 | — | — | — | — |
| (10) | Titanium dioxide | 8.0 | 8.0 | 30.0 | — | 8.0 |
| (11) | Aluminum powder | — | — | — | 30.0 | — |
| (12) | Iron oxide pigment | 2.0 | 2.0 | 2.0 | 2.0 | 2.0 |
| (13) | Sericite | 17.0 | 17.0 | 7.0 | 7.0 | 17.0 |
| (14) | Globular PMMA powder | 9.0 | 9.0 | 9.0 | 9.0 | 9.0 |
| (15) | Fragrance | proper amount | proper amount | proper amount | proper amount | proper amount |
|  | Red-covering power | 10 | 12 | 5.3 | 17.8 | 2 |
|  | Hiding ability | 15 | 7 | 411 | 3,060 | 8 |

[*4]: TiO$_2$-coated mica processed with red iron oxide
[Duocrome YR manufactured by Mearl Corp. with Fe$_2$O$_3$/TiO$_2$/mica = (3–5)/(36–42)/(56–61), optical film thickness of TiO$_2$ at about 250 nm, and transmitted light of blue to green]
[*5]: TiO$_2$-coated mica processed with red iron oxide
[Duocrome YB manufactured by Mearl Corp. with Fe$_2$O$_3$/TiO$_2$/mica = (1–2)/(44–49)/(48–54), optical film thickness of TiO$_2$ at about 310 nm, and transmitted light of yellow to red]
[*6]: 48.0% Fe$_2$O$_3$-coated mica (with transmitted light of blue to green)

Next, the covering effect, transparent feel, and finishing naturalness of thus obtained oily stick foundation samples for adjusting red hyperchromic portions were evaluated. Namely, the samples were applied to 10 people having a hyperchromic portion of a heavy red mark (angioma or the like), a third party observed and judged the results with five steps of 5 (effective or natural) to 1 (ineffective or unnatural), and then an average of thus evaluated values for each evaluation item was obtained.

Further, the skin color (in the normal and hyperchromic portions) was measured in the method previously noted before and after the application to determine the color difference therebetween. Then, an average of thus calculated color differences was calculated for each item. These results are shown in TABLE 5.

TABLE 5

|  | Example | | Comparative Example | | |
|---|---|---|---|---|---|
|  | 3 | 4 | 4 | 5 | 6 |
| Covering effect (Skin-color adjusting effect) | 4.1 | 4.3 | 4.2 | 4.2 | 2.9 |
| Transparent feel | 3.2 | 3.8 | 1.0 | 2.5 | 3.5 |
| Finishing naturalness | 3.7 | 4.1 | 2.3 | 1.9 | 2.1 |
| Color difference (Δ E) | 16.5 | 16.5 | 16.5 | 16.5 | 16.5 |

TABLE 5-continued

| | Example | | Comparative Example | | |
|---|---|---|---|---|---|
| | 3 | 4 | 4 | 5 | 6 |
| between normal naked skin and hyperchromic naked skin Color difference (ΔE) between normal skin and hyperchromic skin after application | 2.2 | 1.6 | 5.8 | 4.3 | 8.2 |

As clearly shown by TABLE 5, the foundation samples of Examples 3 and 4 in which powder having blue to green transmitted light had been compounded in accordance with the present invention not only were excellent in covering red hyperchromic portions of angioma or the like (i.e. in skin-color adjusting effect) but also yielded transparent feel and natural finishing. In particular, Example 4 which used a titanium oxide coated mica having blue to green transmitted coherent light yielded excellent finishing feel which had not conventionally been experienced. Also, when a commercially-available emulsion foundation was applied after the application of these adjusting foundations, the gloss of titanium oxide coated mica could be provided as a natural transparent feel.

On the other hand, Comparative Example 4, in which a large amount of conventionally-used titanium dioxide had been compounded, yielded a powdery finish without transparent feel, while exhibiting a covering effect. Also, though Comparative Example 5, in which aluminum powder was compounded, showed an excellent hiding characteristic, it yielded an unnatural glossy feel in finishing and a roughness was felt when in use. Further, interestingly, Comparative Example 6, which used a titanium oxide coated mica having blue to green reflected light which was in complementary color relationship with Example 4, hardly showed the covering effect, though exhibiting a transparent feel. Therefore, it was unfavorable as an adjusting foundation.

Tests for Hiding Ability, Blue-Covering Power, and Red-Covering Power

1) Hiding-Ability Testing Method
(Sample)

The blue skin-color adjusting composition (S-1) made by Example 2, the red skin-color adjusting composition (S-2) made by Example 4, a commercially-available partial background foundation for covering hyperchromic portions of the skin (Spots Cover manufactured by Shiseido Co., Ltd., R-1), and a commercially-available partial background foundation (manufactured by O'leary Corp., R-2) were used as samples.

(Method)

With a concentration of 80% by weight, each of the above-mentioned samples was mixed into a nitrocellulose vehicle by a small stirrer. Then, an applicator was used to apply this mixture, with a thickness of 30 μm, to a hiding-chart having white and black backgrounds. Thereafter, a Minolta colorimeter CM-1000 was used to measure the color tone values of the sample applied to the white and black backgrounds. Then, the color difference ΔE between thus measured values in the white and black backgrounds was determined. This color difference was used to determine the hiding ability according to the following equation (1):

$$\text{hiding ability} = (1/\Delta E) \times 100 \quad (1)$$

The hiding ability of 1,000, which corresponds to the color difference of 0.1, is a level at which both white and black backgrounds are completely masked. The hiding ability of 100, which corresponds to the color difference of 1.0, is a level at which there is substantially no difference in color tone between white and black backgrounds. The hiding ability of 10, which corresponds to the color difference of 10.0, is a level by which white and black backgrounds can clearly be discerned from each other.

2) Blue-Covering Power Testing Method
(Sample)

Samples S-1, R-1, and R-2 mentioned in the hiding-ability test were used.

(Method)

In a similar manner to that of the hiding-ability test, each sample was applied to a blue transparent PET film. A goniospectrophotometer GCMS-3 manufactured by Murakami Color Lab. was used to conduct colorimetry under the conditions where the incident light angle was 45° and the light-receiving angle was −15°.

Then, the difference between the integrated value of the reflectivity of the blue transparent PET film at the wavelength range of 400–550 nm measured as a control and the integrated value of the reflectivity of the blue transparent PET film coated with the sample at the wavelength range of 400–550 nm was determined by the following equation (3):

$$\text{blue-covering power} = [(X-Y)/X] \times 100 \quad (3)$$

wherein X is an integrated value of the reflectivity of the blue transparent PET film at 400–550 nm without being coated with the skin-color adjusting composition and Y is an integrated value of the reflectivity of the blue transparent PET film at 400–550 nm when coated with the skin-color adjusting composition.

3) Red-Coveting Power Testing Method
(Sample)

Samples S-1, R-1, and R-2 mentioned in the hiding-ability test were used.

(Method)

In a similar manner to that of the blue-covering power test, each sample was applied to a red transparent PET film. A goniospectrophotometer GCMS-3 manufactured by Murakami Color Lab. was used to conduct colorimetry under the conditions where the incident light angle was 45° and the light-receiving angle was −15°.

Then, the difference between the integrated value of the reflectivity of the red transparent PET film at the wavelength range of 600–730 nm measured as a control and the integrated value of the reflectivity of the red transparent PET film coated with the sample at the wavelength range of 600–730 nm was determined by the following equation (2):

$$\text{red-covering power} = [(V-W)/V] \times 100 \quad (2)$$

wherein V is an integrated value of the reflectivity of the red transparent PET film at 600–730 nm without being coated with the skin-color adjusting composition and W is an integrated value of the reflectivity of the red transparent PET film at 600–730 nm when coated with the skin-color adjusting composition.

4) Results

Figure 8:
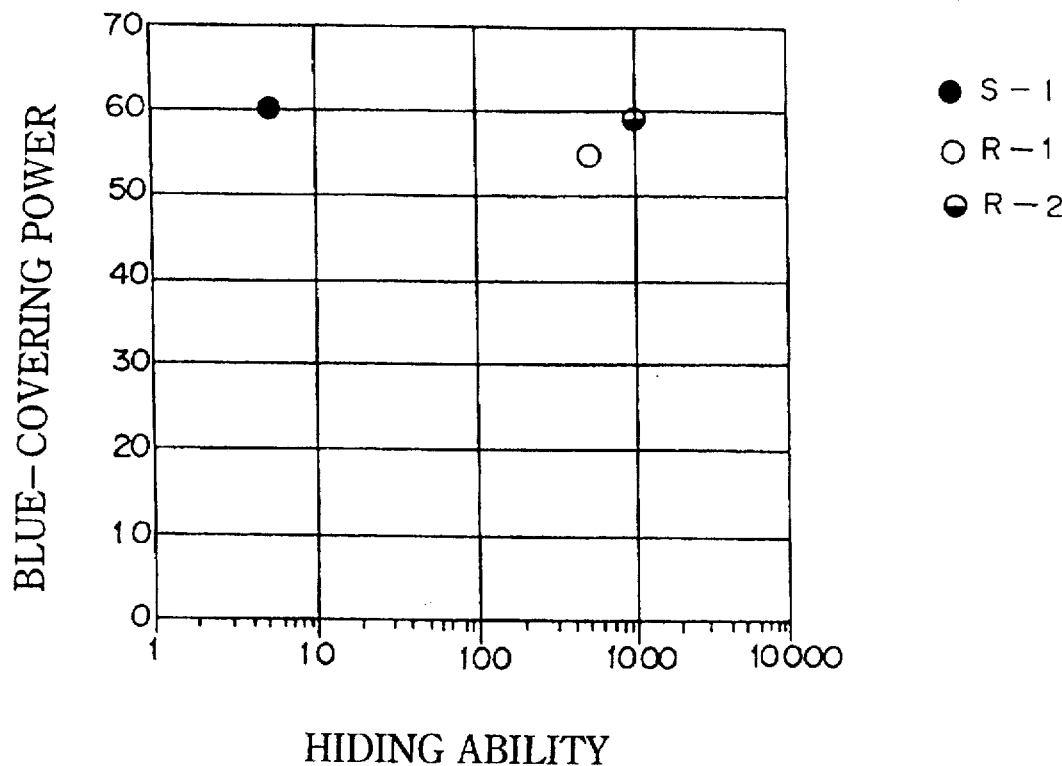
FIG. 8 is a chart comparing the hiding ability and blue-covering power of S-1, which is a blue skin-color adjusting composition in accordance with the present invention, with those of conventional products.
Figure 9:
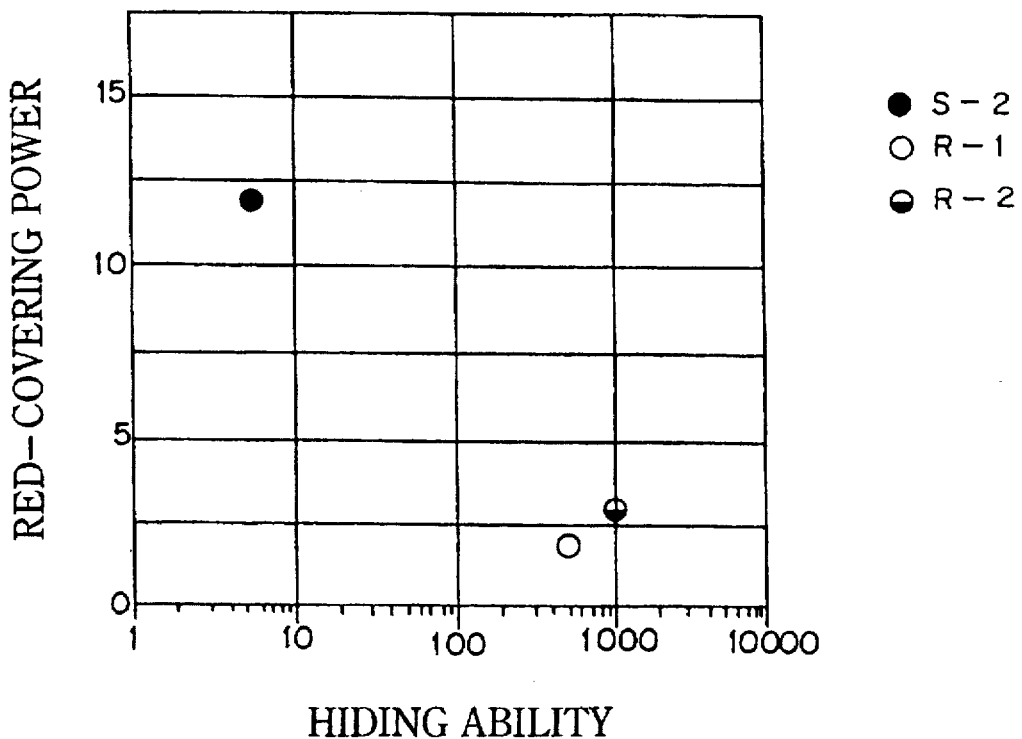
FIG. 9 is a chart comparing the hiding ability and red-covering power of S-2, which is a red skin-color adjusting composition in accordance with the present invention, with those of the conventional products.

FIG. 8 is a chart showing the results of the hiding ability and blue-covering power of S-1, which is the blue skin-color adjusting composition in accordance with the present invention, together with those of the conventional products R-1 and R-2. FIG. 9 is a chart showing the results of the hiding ability and red-covering power of S-2, which is the red skin-color adjusting composition in accordance with the present invention, together with those of the conventional products R-1 and R-2.

In the first place, it is recognized that the conventional partial background foundation products R-1 and R-2 have much higher hiding ability than that of S-1 and S-2. Thus, the conventional products entirely mask hyperchromic portions of the skin to effect color adjustment. On the other hand, S-1 and S-2 have only about several hundredths to several thousandths of the hiding ability as compared with that of the conventional products.

However, FIG. 8 shows that the blue-covering power of S-1, which hardly has the hiding ability, is higher than that of the conventional products R-1 and R-2. Also, FIG. 9 shows that the red-covering power of S-2, which hardly has the hiding ability, is higher than that of the conventional products R-1 and R-2. Accordingly, it is recognized that the skin-color adjusting composition used in the method of the present invention has very high blue- or red-covering power, while its hiding ability is low.

Example 5 and Comparative Examples 7–9

Oily compact foundation samples for adjusting blue hyperchromic portions having compositions shown in TABLE 6 were made in the following method and their blue-covering power and hiding ability values were determined. These results are also shown in TABLE 6.

(Manufacturing Method)

After ingredients (3)–(6) were heated and dissolved, ingredients (7)–(14) were added thereto and dispersed therein in a dispersion mill. The resulting mixture was processed in a TK mill manufactured by Tokushu Kika and heated to 85° C. Then, ingredients (1) and (2), which had been heated, melted, and mixed together at 90° C. beforehand, as well as ingredient (15) were added thereto. After being deaerated, the mixture was charged into a predetermined mid-size plate and left or cooling to yield oily compact foundation samples for adjusting blue hyperchromic portions.

TABLE 6

| Compounding formula | | Example 5 | Comparative Example 7 | Comparative Example 8 | Comparative Example 9 |
|---|---|---|---|---|---|
| (1) | Carnauba wax | 1.0 | 1.0 | 1.0 | 1.0 |
| (2) | Microcrystalline wax | 5.0 | 5.0 | 5.0 | 5.0 |
| (3) | Decamethyl cyclopentasiloxane | 8.5 | 8.5 | 8.5 | 8.5 |
| (4) | Squalane | 21.0 | 21.0 | 21.0 | 21.0 |
| (5) | Cetyl-2-ethylhexanoate | 15.0 | 15.0 | 15.0 | 15.0 |
| (6) | Sorbitan dioleate | 1.5 | 1.5 | 1.5 | 1.5 |
| (7) | Colored titanium oxide coated mica (blue interference color)*[7] | 20.0 | — | — | — |
| (8) | Colored titanium oxide coated mica (red interference color)*[8] | — | — | — | 20.0 |
| (9) | Titanium dioxide | 11.0 | 30.0 | — | 11.0 |
| (10) | Aluminum powder | — | — | 30.0 | — |
| (11) | Red No. 226 | 0.4 | 0.6 | 0.6 | 0.4 |
| (12) | Yellow iron oxide | 1.6 | 1.6 | 2.4 | 1.6 |
| (13) | Mica | 11.0 | 11.0 | 11.0 | 11.0 |
| (14) | Globular nylon | 4.0 | 4.0 | 4.0 | 4.0 |
| (15) | Fragrance | proper amount | proper amount | proper amount | proper amount |
| | Blue-covering power | 68 | 32 | 69 | 55 |
| | Hiding ability | 9 | 527 | 2,852 | 12 |

*[7]: colored titanium oxide coated mica of MANUFACTURING EXAMPLE 1
(color of appearance: skin color; reflected interference color: blue; transmitted interference color: yellow)
*[8]: Duocrome YB manufactured by Mearl Corp.
(color of appearance: skin color; reflected interference color: blue; transmitted interference color: yellow)

Next, the covering effect, transparent feel, and finishing naturalness of thus obtained oily compact foundation samples for adjusting blue hyperchromic portions were evaluated. Namely, the samples were applied to 10 people having a hyperchromic portion of a heavy blue mark (Ota's nevus or the like), a third party observed and judged the results with five steps of 5 (effective or natural) to 1 (ineffective or unnatural), and then an average of thus evaluated values for each evaluation item was obtained.

Further, the skin color (in the normal and hyperchromic portions) was measured by a Minolta colorimeter CM-1000 before and after the application to determine the color difference therebetween. Then, an average of thus measured color differences was calculated for each item.

These results are shown in TABLE 7.

TABLE 7

| | Example | Comparative Example | | |
|---|---|---|---|---|
| | 5 | 7 | 8 | 9 |
| Covering effect (Skin-color adjusting effect) | 4.6 | 4.5 | 4.8 | 4.2 |
| Transparent feel | 4.5 | 1.9 | 2.5 | 3.8 |
| Finishing naturalness | 4.8 | 2.5 | 1.2 | 3.9 |
| Color difference ($\Delta E$) between normal naked skin and hyperchromic naked skin | 18.1 | 18.1 | 18.1 | 18.1 |
| Color difference ($\Delta E$) between normal skin and hyperchromic skin after application | 1.0 | 3.8 | 6.4 | 1.4 |

As clearly shown by TABLE 7, the foundation sample of Example 5, in which the colored titanium oxide coated mica having yellow transmitted light in accordance with the present invention had been compounded, not only was excellent in covering blue hyperchromic portions of Ota's nevus or the like (i.e. in skin-color adjusting effect) but also yielded transparent feel and natural finishing. Also, when a commercially-available powdery foundation was applied after the application of this adjusting foundation, the gloss of titanium oxide coated mica changed into a natural transparent feel so as to yield a finishing feel which was comparable to the normal portion.

On the other hand, Comparative Example 7, in which a large amount of conventionally-used titanium dioxide had been compounded, yielded a powdery finish without transparent feel, while exhibiting a covering effect. Also, though Comparative Example 8, in which aluminum powder had been compounded, showed an excellent hiding characteristic, it yielded an unnatural glossy feel in finishing and a roughness was felt when in use. Further, though Comparative Example 9, which used a commercial titanium oxide coated mica coated with iron oxide, was superior to Comparative Examples 7 and 8 in all the items, it was inferior to Example 5, in which the colored titanium oxide coated mica in accordance with the present invention was used, in the transparent feel and finishing naturalness.

Example 6 and Comparative Examples 10–12

Oily stick foundation samples for adjusting red hyperchromic portions having compositions shown in TABLE 8 were made, in the following method and their red-covering power and hiding ability values were determined. These results are also shown in TABLE 8.

(Manufacturing Method)

After ingredients (3)–(6) were heated and dissolved, ingredients (7)–(14) were added thereto and dispersed therein in a dispersion mill. The resulting mixture was processed in a TK mill manufactured by Tokushu Kika and heated to 85° C. Then, ingredients (1) and (2), which had been heated, melted, and mixed together at 90° C.

beforehand, as well as ingredient (15) were added thereto. After being deaerated, the mixture was charged into a predetermined stick container and then left for cooling to yield stick foundation samples for adjusting red hyperchromic portions.

TABLE 8

| Compounding formula | Example 6 | Comparative Example 10 | Comparative Example 11 | Comparative Example 12 |
|---|---|---|---|---|
| (1) Carnauba wax | 1.0 | 1.0 | 1.0 | 1.0 |
| (2) Solid paraffin wax | 6.0 | 6.0 | 6.0 | 6.0 |
| (3) Dimethylsilicone | 7.5 | 7.5 | 7.5 | 7.5 |
| (4) Liquid paraffin | 15.0 | 15.0 | 15.0 | 15.0 |
| (5) Glyceryl monoisostearate | 20.5 | 20.5 | 20.5 | 20.5 |
| (6) Sorbitan diisostearate | 2.0 | 2.0 | 2.0 | 2.0 |
| (7) Hydrophobically-processed colored titanium oxide coated mica (red interference color)*9 | 12.0 | — | — | — |
| (8) Hydrophobically-processed colored titanium oxide coated mica (blue interference color)*10 | — | — | — | 12.0 |
| (9) Titanium dioxide | 8.0 | 29.0 | — | 8.0 |
| (10) Aluminum powder | — | — | 29.0 | — |
| (11) Yellow oxide pigment | 2.0 | 3.0 | 3.0 | 2.0 |
| (12) Sericite | 17.0 | 7.0 | 7.0 | 17.0 |
| (13) Globular PMMA powder | 9.0 | 9.0 | 9.0 | 9.0 |
| (14) Fragrance | proper amount | proper amount | proper amount | proper amount |
| Red-covering power | 16 | 5.1 | 18.1 | 2 |
| Hiding ability | 8 | 416 | 2,896 | 8 |

*9: colored titanium oxide coated mica of MANUFACTURING EXAMPLE 2
(color of appearance: skin color; reflected interference color: red; transmitted interference color: green)
*10: Duocrome YB manufactured by Mearl Corp.
(color of appearance: skin color; reflected interference color: blue; transmitted interference color: yellow)

Next, the covering effect, transparent feel, and finishing naturalness of thus obtained oily stick foundation samples for adjusting red hyperchromic portions were evaluated Namely, the samples were applied to 10 people having a hyperchromic portion of a heavy red mark (angioma or the like), a third party observed and judged the results with five steps of 5 (effective or natural) to 1 (ineffective or unnatural), and then an average of thus evaluated values for each evaluation item was obtained.

Further, the skin color (in the normal and hyperchromic portions) was measured in the method previously noted before and after the application to determine the color difference therebetween. Then, an average of thus calculated color differences was calculated for each item. These results are shown in TABLE 9.

TABLE 9

| | Example 6 | Comparative Example 10 | Comparative Example 11 | Comparative Example 12 |
|---|---|---|---|---|
| Covering effect (Skin-color adjusting effect) | 4.7 | 4.2 | 4.2 | 2.9 |
| Transparent feel | 4.6 | 1.0 | 2.5 | 3.5 |
| Finishing naturalness | 4.7 | 2.3 | 1.9 | 2.1 |
| Color difference ($\Delta E$) between normal naked skin and hyperchromic naked skin | 16.5 | 16.5 | 16.5 | 16.5 |

TABLE 9-continued

| | Example 6 | Comparative Example 10 | Comparative Example 11 | Comparative Example 12 |
|---|---|---|---|---|
| Color difference ($\Delta E$) between normal skin and hyperchromic skin after application | 1.1 | 5.8 | 4.3 | 8.2 |

As clearly shown by TABLE 9, the foundation sample of Example 6, in which the colored titanium oxide coated mica of MANUFACTURING EXAMPLE 2 having green transmitted light in accordance with the present invention had been compounded, not only was excellent in covering red hyperchromic portions of angiomas or the like (i.e. in skin-color adjusting effect) but also yielded transparent feel and natural finishing. Also, when a commercially-available emulsion foundation was applied to both normal and hyperchromic portions after the application of this adjusting foundation, the gloss of the hyperchromic portions was suppressed so as to yield a finishing feel which was comparable to the normal portion.

On the other hand, Comparative Example 10, in which a large amount of conventionally-used titanium dioxide had been compounded, yielded a powdery finish without transparent feel, while exhibiting a covering effect. Also, though Comparative Example 11, in which aluminum powder had been compounded, showed an excellent hiding characteristic, it yielded an unnatural glossy feel in finishing and a roughness was felt when in use. Further, when in using a commercial titanium oxide coated mica coated with iron oxide having a color of the transmitted coherent light (green) similar to that of the colored titanium coated mica of MANUFACTURING EXAMPLE 2 used in Example 6, was superior to Comparative Examples 10 and 11 in all the items, it was inferior to Example 6, in which the colored titanium oxide coated mica in accordance with the present invention was used, in the transparent feel and finishing naturalness. Also, Comparative Example 12, which used a commercially-available titanium oxide coated mica having yellow transmitted coherent light which was nearly in complementary color relationship with the transmitted coherent light of the colored titanium oxide coated mica of MANUFACTURING EXAMPLE 2 used in Example 6, hardly showed the covering effect, though exhibiting a transparent feel. Therefore, it was unfavorable as an adjusting foundation.

Tests for Hiding Ability, Blue-Covering Power, and Red-Covering Power
1) Hiding-Ability Testing Method
(Sample)
The blue skin-color adjusting composition (S-3) made by Example 5, the red skin-color adjusting composition (S-4) made by Example 6, a commercially-available partial background foundation for covering hyperchromic portions of the skin (Spots Cover manufactured by Shiseido Co., Ltd., R-1), and a commercially-available partial background foundation (manufactured by C Corp., R-2) were used as samples.
(Method)
It is treated in the same way as previously described method.
2) Blue- Covering Power Testing Method
(Sample)
Samples S-3, R-1, and R-2 mentioned in the hiding-ability test were used.

(Method)

It is treated in the same way as previously described method.

3) Red-Covering Power Testing Method (Sample)

Samples S-4, R-1, and R-2 mentioned in the hiding-ability test were used.

(Method)

It is treated in the same way as previously described method.

4) Results

Figure 10:
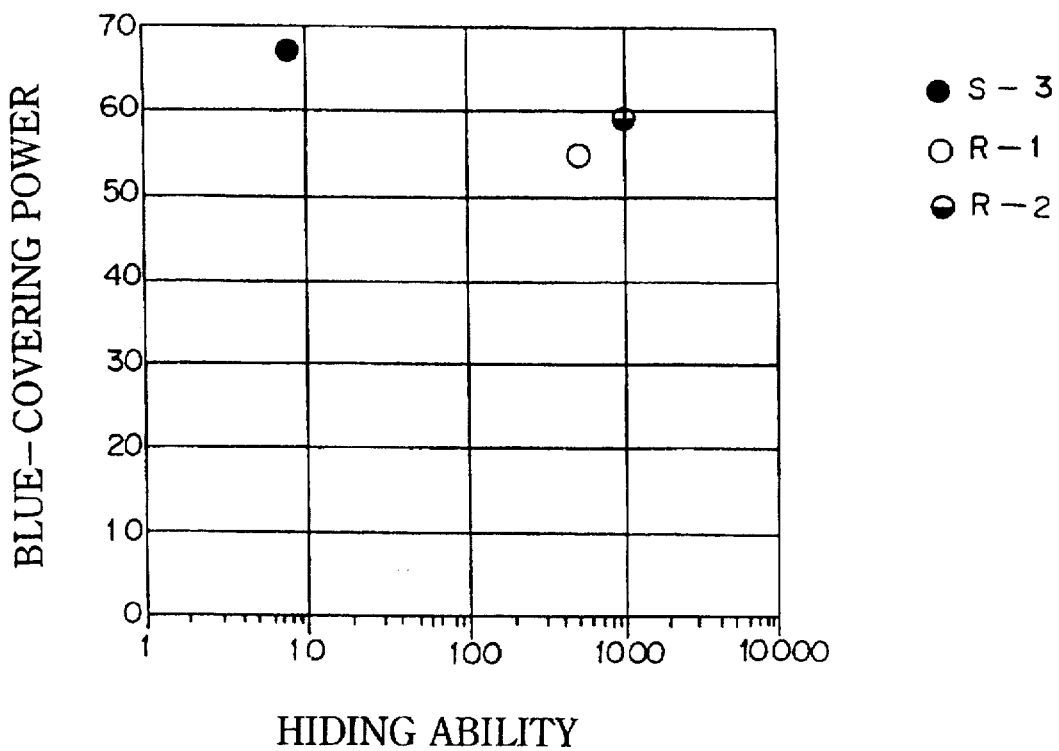
FIG. 10 is a chart comparing the hiding ability and blue-covering power of S-3, which is a blue skin-color adjusting composition in accordance with the present invention, with those of the conventional products.
Figure 11:
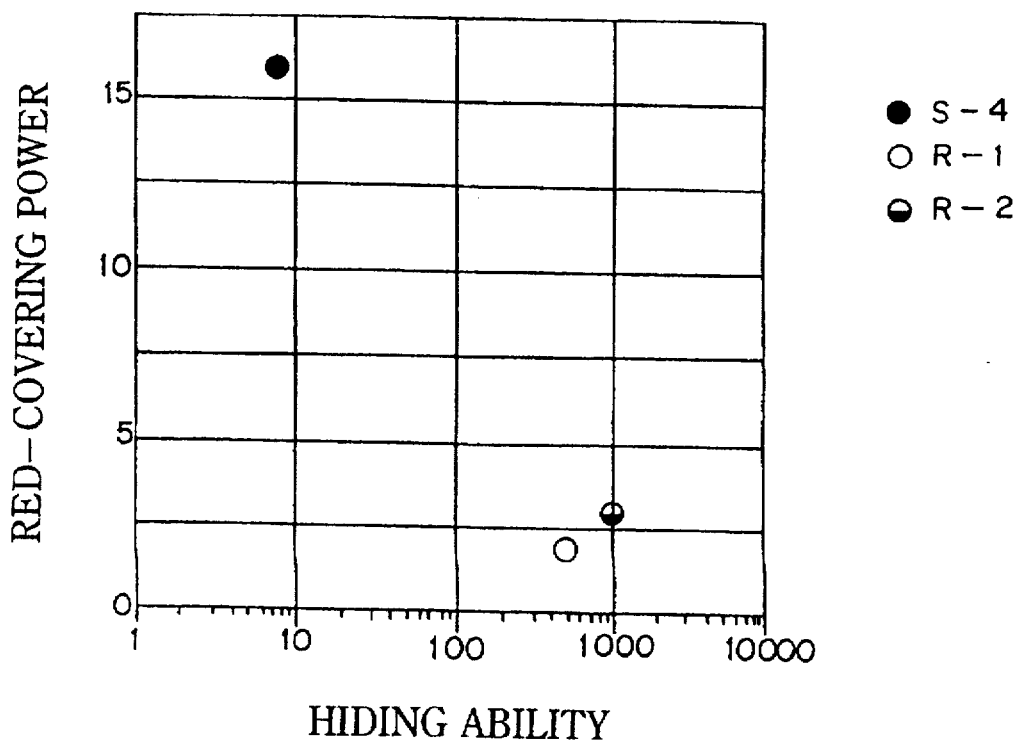
FIG. 11 is a chart comparing the hiding ability and red-covering power of S-4, which is a red skin-color adjusting composition in accordance with the present invention, with those of the conventional products.

FIG. 10 is a chart showing the results of the hiding ability and blue-covering power of S-3, which is the blue skin-color adjusting composition in accordance with the present invention, together with those of the conventional products R-1 and R-2. FIG. 11 is a chart showing the results of the hiding ability and red-covering power of S-4, which is the red skin-color adjusting composition in accordance with the present invention, together with those of the conventional products R-1 and R-2.

In the first place, it is recognized that the conventional partial background foundation products R-1 and R-2 have much higher hiding ability than that of S-3 and S-4. Thus, the conventional products entirely mask hyperchromic portions of the skin to effect color adjustment. On the other hand, S-3 and S-4 have only about several hundredths to several thousandths of the hiding ability as compared with that of the conventional products.

However, FIG. 10 shows that the blue-covering power of S-3, which hardly has the hiding ability, is higher than that of the conventional products R-1 and R-2. Also, FIG. 11 shows that the red-Covering power of S-4, which hardly has the hiding ability, is higher than that of the conventional products R-1 and R-2. Accordingly, it is recognized that the skin-color adjusting composition used in the method of the present invention has very high blue- and red-covering powers, while its hiding ability is low.

Also, when S-1, in which the titanium oxide coated mica having yellow to red transmitted coherent light has been compounded in accordance with Example 2, is compared with S-3, in which the colored titanium oxide coated mica of MANUFACTURING EXAMPLE 1 has been compounded, the latter has a blue-covering power higher than that of the former though there is substantially no difference between their hiding ability values.

Similarly, when S-2, in which the titanium oxide coated mica having blue to green transmitted coherent light has been compounded in accordance with Example 4, is compared with S-4, in which the colored titanium oxide coated mica of MANUFACTURING EXAMPLE 2 has been compounded, the latter has a red-covering power higher than that of the former though there is substantially no difference between their hiding ability values.

Accordingly, when the samples in which the colored titanium oxide coated mica obtained by MANUFACTURING EXAMPLES 1 and 2 of the present invention has been compounded is compared with those without these materials, the former exhibit relatively higher blue-covering power or red-covering power though their hiding ability is lower. This point will also be clearly understood from the following Examples.

Example 7: Water-in-Oil Type Emulsion Foundation for Adjusting Blue Hyperchromic Portion (Compounding Formula)

| | | |
|---|---|---|
| (1) | Decamethyl cyclopentasiloxane | 27.0% by weight |
| (2) | Dimethyl polysiloxane | 3.0 |
| (3) | Polyoxyalkylene-modified organopolysiloxane | 2.0 |
| (4) | Titanium oxide coated mica processed with dextrin fatty-acid ester (blue interference color) | 18.0 |
| (5) | Titanium dioxide processed with dextrin fatty-acid ester | 4.0 |
| (6) | Iron oxide pigment processed with dextrin fatty-acid ester | 2.0 |
| (7) | Paraben | 0.2 |
| (8) | 1,3-butylene glycol | 4.0 |
| (9) | Ion-exchanged water | remainder |

(Timilon Blue MP-155 manufactured by Merck Corp. with TiO$_2$/mica = (48–53)/(47–52), optical film thickness of TiO$_2$ at about 310 nm, and transmitted light of yellow to red)

(Manufacturing Method)

After ingredients (1)–(3) were stirred and mixed together, ingredients (4)–(6) were added thereto and dispersed therein. Then, an aqueous phase portion, which was composed of ingredients (7) and (8) melted into ingredient (9), was added to the mixture. The resulting mixture was emulsified to yield a water-in-oil type emulsion foundation for adjusting blue hyperchromic portion having a hiding ability, of 10 and a blue-covering power of 55.

(Effect)

When applied to a panel having a blue hyperchromic portion of Ota's nevus, this foundation effectively adjusted the hyperchromic portion and exhibited an excellent hiding effect, while yielding a transparent feel in finishing. When a commercially-available solid face powder product was applied to the normal portion and the hyperchromic portion thus coated with the foundation, the gloss of the hyperchromic portion caused by the foundation was suppressed so that substantially no difference was perceived between these portions, thereby yielding a natural feel in finishing.

Example 8: Water-in-Oil Type Emulsion Stick Foundation for Adjusting Red Hyperchromic Portion Compounding Formula)

| | | |
|---|---|---|
| (1) | Decamethyl cyclopentasiloxane | 38.0% by weight |
| (2) | Polyethylene wax | 10.0 |
| (3) | Carnauba wax | 1.0 |
| (4) | Polyoxyalkylene-modified organopolysiloxane | 0.5 |
| (5) | Sorbitan sesquiisostearate | 1.5 |
| (6) | Titanium oxide coated mica processed with silicone (red interference color) | 5.0 |
| (7) | Talc processed with silicone | 2.0 |
| (8) | Sericite processed with silicone | 10.0 |
| (9) | Titanium dioxide processed with silicone | 9.0 |
| (10) | Red iron oxide processed with silicone | 1.0 |
| (11) | Yellow iron oxide processed with silicone | 2.0 |
| (12) | Globular nylon powder | 5.0 |
| (13) | Paraben | 0.1 |
| (14) | Fragrance | proper amount |

| (15) | 1,3-butylene glycol | 4.0 |
| (16) | Ion-exchanged water | remainder |

(Timica Iridescent Red manufactured by Mearl Corp. with $TiO_2$/mica = (39–45)/(55–61), optical film thickness of $TiO_2$ at about 250 nm, and transmitted light of blue to green)

(Manufacturing Method)

After ingredients (1)–(5) and (14) were heated and melted at 90° C., ingredients (6)–(12) were added thereto and dispersed therein by a homogenizer. Then, a mixture of ingredients (13), (15), and (16) which had been heated to 95° C. was added thereto and the resulting mixture was emulsified. Thus formed emulsion was charged into a predetermined stick container and cooled to room temperature to yield a water-in-oil type emulsion stick foundation for adjusting red hyperchromic portion having a hiding ability of 9 and a red-covering power of 11.

(Effect)

This water-in-oil type emulsion stick foundation not only effectively covered heavy red hyperchromic portions of angioma or the like with a transparent feel in finishing but also was effective in adjusting light red hyperchromic portions such as acne scars and red face.

Example 9: Powdery Foundation for Adjusting Light Red Hyperchromic Portion (Compounding Formula)

| (1) | Talc | 20.0% by weight |
| (2) | Sericite | 38.8 |
| (3) | Titanium oxide coated mica (red interference color) | 9.0 |
| (4) | Titanium dioxide | 11.0 |
| (5) | Globular polystyrene | 5.0 |
| (6) | Red iron oxide | 0.6 |
| (7) | Yellow iron oxide | 1.8 |
| (8) | Black iron oxide | 0.1 |
| (9) | D&C Red No. 30 | 0.2 |
| (10) | Paraben | 0.5 |
| (11) | Liquid paraffin | 5.0 |
| (12) | Dimethylsilicone | 5.0 |
| (13) | Sorbitan monoisostearate | 2.0 |
| (14) | Ceresin | 1.0 |

(Duocrome YR manufactured by Mearl Corp. with blue-green transmitted light)

(Manufacturing Method)

Ingredients (1)–(9) were stirred and mixed. To this mixture, ingredients (10)–(14) which had been heated and melted were added and then mixed and dispersed therein. The resulting mixture was pulverized in a pulverizer and then compacted in a mid-size plate to yield a powdery foundation for adjusting light red hyperchromic portions having a hiding ability of 14 and a red-cover power of 12.

(Effect)

When applied to a panel whose face has a light red portion of acne scars, red face, or the like, this foundation effectively adjusted the hyperchromic portion and yielded a natural feel in finishing which was similar to the naked normal skin.

Example 10: Water-in-Oil Type Emulsion Foundation for Adjusting Blue Hyperchromic Portion (Compounding Formula)

| (1) | Decamethyl cyclopentasiloxane | 27.0% by weight |
| (2) | Dimethyl polysiloxane | 3.0 |
| (3) | Polyoxyalkylene-modified organopolysiloxane | 2.0 |
| (4) | Colored titanium oxide coated mica processed with dextrin fatty-acid ester (blue interference color) | 18.0 |
| (5) | Titanium dioxide processed with dextrin fatty-acid ester | 4.0 |
| (6) | Iron oxide pigment processed with dextrin fatty-acid ester | 2.0 |
| (7) | Paraben | 0.2 |
| (8) | 1,3-butylene glycol | 4.0 |
| (9) | Ion-exchanged water | reminder |

(colored titanium oxide coated mica of MANUFACTURING EXAMPLE 1 being processed with dextrin fatty-acid ester)

(Manufacturing Method)

After ingredients (1)–(3) were stirred and mixed together, ingredients (4)–(6) were added thereto and dispersed therein. Then, an aqueous phase portion, which was composed of ingredients (7) and (8) melted into ingredient (9), was added to the mixture. The resulting mixture was emulsified to yield a water-in-oil type emulsion foundation for adjusting blue hyperchromic portion having a hiding ability of 12 and a blue-covering power of 65.

(Effect)

When applied to a panel having a blue hyperchromic portion of Ota's nevus, this foundation effectively adjusted the hyperchromic portion and exhibited an excellent hiding effect, while yielding a transparent feel in finishing. When a commercially-available solid face powder product was applied to the normal portion and the hyperchromic portion thus coated with the foundation, the gloss of the hyperchromic portion caused by the foundation was suppressed so that substantially no difference was perceived between these portions, thereby yielding a natural feel in finishing.

Further, this foundation yielded higher blue-covering power and more natural finishing feel than those of Example 7, while there was not a large difference between their hiding ability values.

Example 11: Water-in Oil Type Emulsion Stick Foundation for Adjusting Red Hyperchromic Portion (Compounding Formula)

| (1) | Decamethyl cyclopentasiloxane | 38.0% by weight |
| (2) | Polyethylene wax | 10.0 |
| (3) | Carnauba wax | 1.0 |
| (4) | Polyoxyalkylene-modified organopolysiloxane | 0.5 |
| (5) | Sorbitan sesquiisostearate | 1.5 |
| (6) | Colored titanium oxide coated mica processed with silicone (red interference color) | 5.0 |
| (7) | Talc processed with silicone | 2.0 |
| (8) | Sericite processed with silicone | 10.0 |
| (9) | Titanium dioxide processed with silicone | 9.0 |
| (10) | Red iron oxide processed with silicone | 1.0 |
| (11) | Yellow iron oxide processed with silicone | 2.0 |
| (12) | Globular nylon powder | 5.0 |
| (13) | Paraben | 0.1 |
| (14) | Fragrance | proper amount |

-continued

| | | |
|---|---|---|
| (15) | 1,3-butylene glycol | 4.0 |
| (16) | Ion-exchanged water | remainder |

(colored titanium oxide coated mica of MANUFACTURING EXAMPLE 2 being processed with silicone)

(Manufacturing Method)

After ingredients (1)–(5) and (14) were heated and melted at 90° C., ingredients (6)–(12) were added thereto and dispersed therein by a homogenizer. Then, a mixture of ingredients (13), (15), and (16) which had been heated to 95° C. was added thereto and the resulting mixture was emulsified. Thus formed emulsion was charged into a predetermined stick container and coded to room temperature to yield a water-in-oil type emulsion stick foundation for adjusting red hyperchromic portion having a hiding ability of 10 and a red-covering power of 14.

(Effect)

This water-in-oil type emulsion stick foundation not only effectively covered heavy red hyperchromic portions of angioma or the like with a transparent feel in finishing but also was effective in adjusting light red hyperchromic portions such as acne scars and red face.

Further, this foundation yielded slightly higher red-covering power than that of Example 8, while there was not a large difference between their hiding ability values.

Example 12: Powdery Foundation for Adjusting Light Red Hyperchromic Portion (Compounding Formula)

| | | |
|---|---|---|
| (1) | Talc | 20.0% by weight |
| (2) | Sericite | 38.8 |
| (3) | Colored titanium oxide coated mica (red interference color) | 9.0 |
| (4) | Titanium dioxide | 11.0 |
| (5) | Globular polystyrene | 5.0 |
| (6) | Red iron oxide | 0.6 |
| (7) | Yellow iron oxide | 1.8 |
| (8) | Black iron oxide | 0.1 |
| (9) | D&C Red No. 30 | 0.2 |
| (10) | Paraben | 0.5 |
| (11) | Liquid paraffin | 5.0 |
| (12) | Dimethylsilicone | 5.0 |
| (13) | Sorbitan monoisostearate | 2.0 |
| (14) | Ceresin | 1.0 |

(colored titanium oxide coated mica of MANUFACTURING EXAMPLE 2)

(Manufacturing Method)

Ingredients (1)–(9) were stirred and mixed. To this mixture. ingredients (10)–(14) which had been heated and melted were added and then mixed and dispersed therein. The resulting mixture was pulverized in a pulverizer and then compacted in a mid-size plate to yield a powdery foundation for adjusting light red hyperchromic portions having a hiding ability of 17 and a red-cover power of 14.

(Effect)

When applied to a panel whose face has a light red portion of acne scars, red face, or the like, this foundation effectively adjusted the hyperchromic portion and yielded a natural feel in finishing which was similar to the naked normal skin.

Example 13: Powdery Foundation for Adjusting Light Blue Hyperchromic Portion (Compounding Formula)

| | | |
|---|---|---|
| (1) | Talc | 20.0% by weight |
| (2) | Sericite | 38.8 |
| (3) | Colored titanium oxide coated mica (blue interference color) | 9.0 |
| (4) | Titanium dioxide | 11.0 |
| (5) | Globular polystyrene | 5.0 |
| (6) | Red iron oxide | 0.6 |
| (7) | Yellow iron oxide | 1.8 |
| (8) | Black iron oxide | 0.1 |
| (9) | D&C Red No. 30 | 0.2 |
| (10) | Paraben | 0.5 |
| (11) | Liquid paraffin | 5.0 |
| (12) | Dimethylsilicone | 5.0 |
| (13) | Sorbitan monoisostearate | 2.0 |
| (14) | Ceresin | 1.0 |

(colored titanium oxide coated mica of MANUFACTURING EXAMPLE 1)

(Manufacturing Method)

Ingredients (1)–(9) were stirred and mixed. To this mixture. ingredients (10)–(14) which had been heated and melted were added and then mixed and dispersed therein. The resulting mixture was pulverized in a pulverizer and then compacted in a mid-size plate to yield a powdery foundation for adjusting light blue hyperchromic portions having a hiding ability of 15 and a blue-cover power of 52.

(Effect)

When applied to a panel whose face has a light blue portion, this foundation effectively adjusted the hyperchromic portion and yielded a natural feel in finishing which was similar to the naked normal skin.

As explained in the foregoing, in the skin-color adjusting method and skin-color adjusting composition in accordance with the present invention, without masking the hyperchromic portion of the skin by hiding ability as in the case of the prior art, the hyperchromic portion of the skin is coated with a composition in which a coherent material has been compounded and, while its hiding ability is low, its interference action can be used to naturally make the hyperchromic portion of the skin inconspicuous without deteriorating the transparent feel of the skin.

Further, in the colored titanium oxide coated mica in which that material is compounded, in accordance with the present invention, since the absorption of light by iron oxide on the surface is so small that the transmitted interference color is not weakened, the coherent material can be used for adjusting the skin color by sufficiently utilizing its filtering effect so as to make hyperchromic portions of the skin inconspicuous.

What is claimed is:

1. A method of adjusting a skin color comprising:
   (a) using a material having a coherent light component, and
   (b) adjusting said coherent light component to a wavelength so as to make a hyperchromic portion of the skin inconspicuous due to an interference action.

2. A method according to claim 1, wherein said material has a transmitted light component which has a wavelength adjusted so as to have a transmitted interference color which is a complementary color for the color of said hyperchromic portion of the skin and is coated on the skin as to make said hyperchromic portion inconspicuous.

3. A skin-color adjusting composition for making a hyperchromic portion of the skin inconspicuous, said composition comprising a material having, as a transmitted light component, a color gamut which is a complementary color for the skin color to be adjusted or in proximity to said complementary color.

4. A composition according to claim 3, wherein said material is compounded with an amount not less than 10% by weight with respect to the whole powder amount in said composition.

5. A composition according to claim 3 wherein said material is titanium oxide coated mica.

6. A skin-color adjusting composition for making a red hyperchromic portion of the skin inconspicuous, in which a material whose transmitted light component has a maximum peak at a wavelength range of 400–550 nm (blue to green) is coated on the skin.

7. A composition according to claim 6, wherein said material is compounded with an amount not less than 10% by weight with respect to the whole powder amount in said composition.

8. A composition according to claim 6 wherein said material comprises titanium dioxide having an optical film thickness of 190–270 nm or 405–500 nm coated on mica.

9. A composition according to claim 6 wherein said material has a hiding ability of not more than 100 determined by the following measuring method A and a red-covering power not less than 8 determined by the following measuring method B:

A: With a concentration of 80% by weight, the skin-color adjusting composition is mixed with a nitrocellulose vehicle; this mixture is applied, with a thickness of 30 μm, to a hiding-chart having white and black backgrounds; and then the color difference ΔE between measured values in the white and black backgrounds is used to determine the hiding ability according to the following equation (1):

$$\text{hiding ability} = (1/\Delta E) \times 100 \tag{1}$$

B: With a concentration of 80% by weight, the skin-color adjusting composition is mixed with a nitrocellulose vehicle; this mixture is applied, with a thickness of 30 μm, to a red transparent PET film; colorimetry is conducted with an incident light angle of 45° and a light-receiving angle of −15°; and then the red-covering power is determined by the following equation (2):

$$\text{red-covering power} = [(V-W)/V] \times 100 \tag{2}$$

wherein V is an integrated value of the reflectivity of the red transparent PET film at 600–730 nm without being coated with the skin-color adjusting composition and W is an integrated value of the reflectivity of the red transparent PET film at 600–730 nm when coated with the skin-color adjusting composition.

10. A composition according to claim 9, wherein the red-covering power is not less than 10.

11. A skin-color adjusting composition for making a blue hyperchromic portion of the skin inconspicuous, in which a material whose transmitted light component has a minimum peak at a wavelength range of 400–550 nm (yellow to red) is compounded.

12. A composition according to claim 11, wherein said material is compounded with an amount not less than 10% by weight with respect to the whole powder amount of said composition.

13. A composition according to claim 11, wherein said material comprises titanium dioxide having an optical film thickness of 290–380 nm or 530–660 nm coated on mica.

14. A composition according to claim 11 wherein said material has a hiding ability of not more than 100 determined by the following measuring method A and a blue-covering power not less than 40 determined by the following measuring method C:

A: With a concentration of 80% by weight, the skin-color adjusting composition is mixed with a nitrocellulose vehicle; this mixture is applied, with a thickness of 30 μm, to a hiding-chart having white and black backgrounds; and then the color difference ΔE between measured values in the white and black backgrounds is used to determine the hiding ability according to the following equation (1):

$$\text{hiding ability} = (1/\Delta E) \times 100 \tag{1}$$

C: With a concentration of 80% by weight, the skin-color adjusting composition is mixed with a nitrocellulose vehicle; this mixture is applied, with a thickness of 30 μm, to a blue transparent PET film; colorimetry is conducted with an incident light angle of 45° and a light-receiving angle of −15°; and then the blue-covering power is determined by the following equation (3):

$$\text{blue-covering power} = [(X-Y)/X] \times 100 \tag{3}$$

wherein X is an integrated value of the reflectivity of the blue transparent PET film at 400–550 nm without being coated with the skin-color adjusting composition and Y is an integrated value of the reflectivity of the red transparent PET film at 400–550 nm when coated with the skin-color adjusting composition.

15. A composition according to claim 9, wherein the blue-covering power is not less than 45.

16. A colored titanium oxide coated mica comprising a fine particle of iron oxide having an average particle diameter of 60–150 nm coated on titanium oxide coated mica.

17. A colored titanium oxide coated mica according to claim 16, wherein the ratio of titanium oxide coated mica (A) and iron oxide free particle (B) is within the range of (A):(B)=(99.5:0.5)–(90:10).

18. A method of making a colored titanium oxide coated mica comprising the step of coating a fine particle of iron oxide having an average particle diameter of 60–150 nm on titanium oxide coated mica.

19. A cosmetic preparation containing a colored titanium oxide coated mica which comprises a fine particle of iron oxide having an average particle diameter of 60–150 m coated on titanium oxide coated mica.

20. A cosmetic preparation according to claim 19, wherein not less than 10% by weight of said colored titanium oxide coated mica is compounded with respect to the whole powder amount of said preparation.

21. A skin-color adjusting composition for making a hyperchromic portion of the skin inconspicuous, said composition comprising a colored titanium oxide coated mica having, as a transmitted light component, a color which is a complementary color for the skin color to be adjusted, said material comprising a fine particle of iron oxide having an average particle diameter of 60–150 nm coated on titanium oxide coated mica.

22. A skin-color adjusting composition for making a red hyperchromic portion of the skin inconspicuous, said composition comprising a colored titanium oxide coated mica, said titanium oxide coated mica composed of titanium dioxide having an optical film thickness of 190–270 nm or 405–500 nm coated on mica and a fine particle of iron oxide having an average particle diameter of 60–150 nm coated thereon.

23. A skin-color adjusting composition for making a blue hyperchromic portion of the skin inconspicuous, said composition comprising a colored titanium oxide coated mica, said titanium oxide coated mica composed of titanium dioxide having an optical film thickness of 290–380 nm or 530–660 nm coated on mica and a fine particle of iron oxide having an average particle diameter of 60–150 nm coated thereon.

24. A composition according to claim 21 wherein not less than 15% by weight of the colored titanium oxide coated mica is compounded with respect to the whole powder amount of said composition.

25. A composition according to claim 3 wherein said transmitted light component is a transmitted coherent light component.

26. A composition according to claim 6, wherein said transmitted light component is a transmitted coherent light component.

27. A composition according to claim 11, wherein said transmitted light component is a transmitted coherent light component.

28. A composition according to claim 21, wherein said transmitted light component is a transmitted coherent light component.

29. A method of covering a hyperchromic portion of skin comprising:
(a) adding a coherent light component to a composition, and
(b) applying said composition to said hyperchromic portion of said skin to make said hyperchromic portion inconspicuous.

30. The method according to claim 29, wherein said composition emitted a transmitted light component whose wavelength is a complementary color of said hyperchromic portion of the skin so as to make said hyperchromic portion inconspicuous.

31. A method of making a colored titanium oxide coated mica comprises the steps of:
(a) dissolving an inorganic or organic iron compound in an aqueous solution,
(b) adding a titanium oxide coated mica to said aqueous solution to form a mixture with said titanium oxide coated mica dispersed in said aqueous solution,
(c) adjusting said mixture to pH to 5.6–7.0 with an alkali,
(d) heating said mixture to 50°–100° C., and
(e) adjusting said mixture to pH 8.0–9.5 with said alkali to completely neutralize and decompose said iron compound.

32. The method of making a colored titanium oxide coated mica according to claim 31, further comprising a step of firing said aqueous solution containing said titanium oxide coated mica and said iron compound to 150° C. to make said titanium oxide coated mica coated with fine particles of iron oxide whose nucleus is said fine particles of iron oxide.

33. The method of making a colored titanium oxide coated mica according to claim 31, further comprising urea in said iron compound containing aqueous solution.

34. The method of making a colored titanium oxide coated mica according to claim 31, wherein said alkali is selected from the group consisting of caustic soda, caustic potash, and aqueous ammonia.

35. The method of making a colored titanium oxide coated mica according to claim 31, wherein said organic or organic iron compound is selected from the group consisting of ferrous chloride, ferric chloride, ferrous sulfate, ferric sulfate, ferrous nitrate, ferric nitrate, ferrous oxalate, ammonium ferric oxalate, ammonium ferric sulfate, ferric phosphate, ferric citrate, ferrous lactate, and iron fumarate.

* * * * *